(12) United States Patent
Zhao et al.

(10) Patent No.: US 9,944,616 B2
(45) Date of Patent: Apr. 17, 2018

(54) PROCESSES FOR THE PREPARATION OF TASIMELTEON AND INTERMEDIATES THEREOF

(71) Applicant: Apotex Inc., Toronto (CA)

(72) Inventors: Yajun Zhao, Brantford (CA); Murali Kondamreddy, Brantford (CA); Peter Garth Blazecka, Brantford (CA); Gamini Weeratunga, Ancaster (CA); Craig Stewart, Edmonton (CA); Nalini Nagireddy, Brantford (CA); Michael B. Johansen, Cambridge (CA); Uma Kotipalli, Brantford (CA)

(73) Assignee: Apotex Inc., Toronto, Ontario (CA)

( * ) Notice: Subject to any disclaimer, the term of this patent is extended or adjusted under 35 U.S.C. 154(b) by 0 days.

(21) Appl. No.: 15/615,020

(22) Filed: Jun. 6, 2017

(65) Prior Publication Data

US 2017/0355688 A1    Dec. 14, 2017

Related U.S. Application Data

(60) Provisional application No. 62/347,190, filed on Jun. 8, 2016.

(51) Int. Cl.
  *C07D 307/79*  (2006.01)
  *C07C 233/05*  (2006.01)
  (Continued)

(52) U.S. Cl.
  CPC .......... *C07D 307/79* (2013.01); *C07B 41/06* (2013.01); *C07C 13/04* (2013.01); *C07C 233/05* (2013.01); *C07C 2602/02* (2017.05)

(58) Field of Classification Search
  CPC ....... C07D 307/79; C07B 41/06; C07C 13/04; C07C 233/05; C07C 2602/02
  (Continued)

(56) References Cited

U.S. PATENT DOCUMENTS

| 5,856,529 A | 1/1999 | Catt et al. |
| 2007/0270593 A1 | 11/2007 | Pereira et al. |

FOREIGN PATENT DOCUMENTS

| CN | 102675268 A | 9/2012 |
| CN | 104327022 A | 2/2015 |

(Continued)

OTHER PUBLICATIONS

Fogassy; Org. Biomol. Chem., 2006, 4, 3011-3030. (Year: 2006).*
(Continued)

*Primary Examiner* — Daniel R Carcanague

(74) *Attorney, Agent, or Firm* — The Webb Law Firm

(57) ABSTRACT

The present invention provides processes for the preparation of Tasimelteon (1), as well as processes for the preparation of intermediates of Formulas (2), (3) and (4) useful in the preparation of Tasimelteon (1).

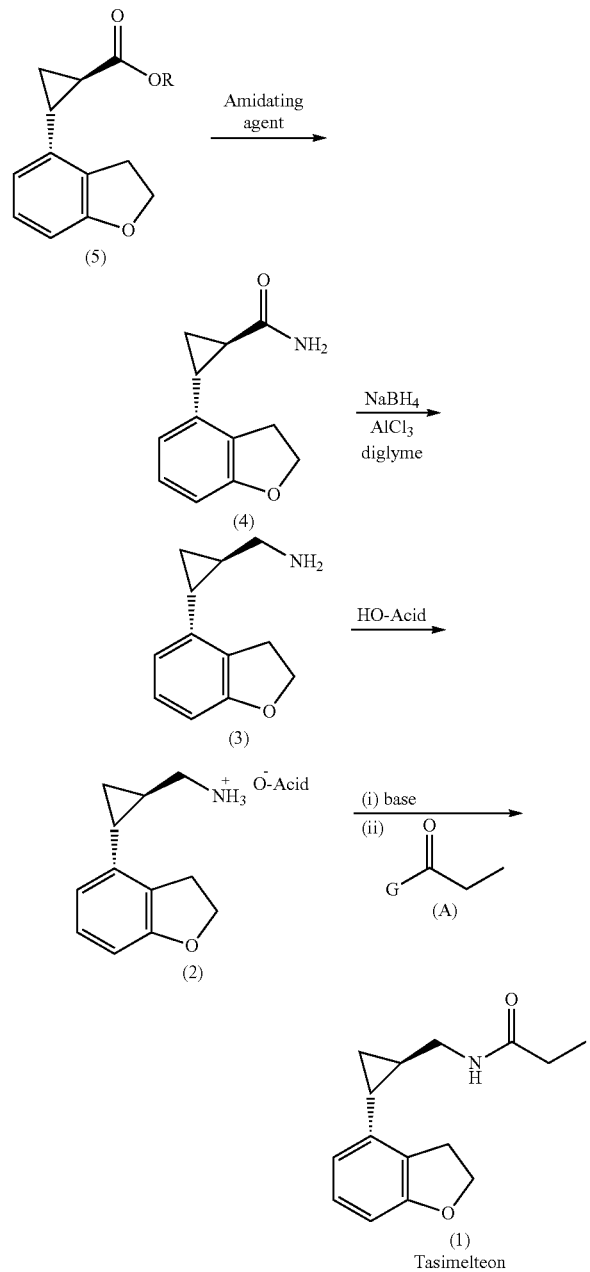

R = $C_1$—$C_4$ alkyl
G = Leaving group
HO-Acid = Optically pure acid

20 Claims, No Drawings

(51) Int. Cl.
*C07C 13/04* (2006.01)
*C07B 41/06* (2006.01)
(58) Field of Classification Search
USPC .......................................... 549/456
See application file for complete search history.

(56) References Cited

FOREIGN PATENT DOCUMENTS

| CN | 106543119 A | 3/2017 |
|----|-------------|--------|
| WO | 9825606 A1 | 6/1998 |
| WO | 2015123389 A1 | 8/2015 |

OTHER PUBLICATIONS

Mi et al., "A facile and practical synthesis of (−)-tasimelteon", Journal of Chemical Research, 2016, pp. 667-669, vol. 10.
Prasad et al., "Development of Jacobsen Asymmetric Epoxidation and Sharpless Asymmetric Dihydroxylation Methods for the Large-Scale Preparation of a Chiral Dihydrobenzofuran Epoxide", Organic Process Research & Development, 2003, pp. 821-827, vol. 7.
Singh et al., "Development of a Practical, Safe, and High-Yielding Process for the Preparation of Enantiomerically Pure trans-Cyclopropane Carboxylic Acid", Organic Process Research & Development, 2002, pp. 618-620, vol. 6.

* cited by examiner

PROCESSES FOR THE PREPARATION OF TASIMELTEON AND INTERMEDIATES THEREOF

CROSS-REFERENCE TO RELATED APPLICATION

This application claims priority to U.S. Provisional Patent Application No. 62/347,190, filed Jun. 8, 2016, the disclosure of which is hereby incorporated in its entirety by reference.

TECHNICAL FIELD

The present invention relates to processes for the preparation of Tasimelteon and intermediates used in the preparation thereof.

BACKGROUND

Tasimelteon, marketed in the United States as HETLIOZ® for the treatment of Non-24-Hour Sleep-Wake Disorder, is a melatonin receptor agonist having the chemical name N-{[(1R,2)-2-(2,3-dihydro-1-benzofuran-4-yl)cyclopropyl]methyl}propanamide, and the following structural formula (1):

(1)

A preparation of Tasimelteon is described in WO 98/25606 A1, which discloses a family of substituted benzodioxole, benzofuran, dihydrobenzofuran and benzodioxanes and their derivatives that are useful as melatonergic agents. Tasimelteon is prepared by the reaction of amine (3) and propionyl chloride, as shown in Scheme 1.

Scheme 1 (Prior Art)

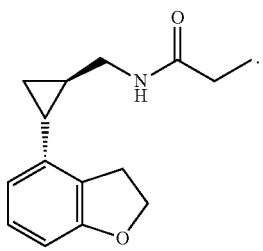

In WO 98/25606 A1, amine (3) is prepared as the fumarate salt (III) by a lengthy sequence, shown in Scheme 2, that includes an asymmetric cyclopropanation using (−)-2,10-camphorsultam as a covalent chiral auxiliary and 1-methyl-3-nitro-1-nitrosoguanidine as a cyclopropanating agent. However, neither the basic chiral auxiliary nor many of the reagents, including the cyclopropanating agent, employed in this process is particularly suitable for use in industrial scale production.

Scheme 2 (Prior Art)

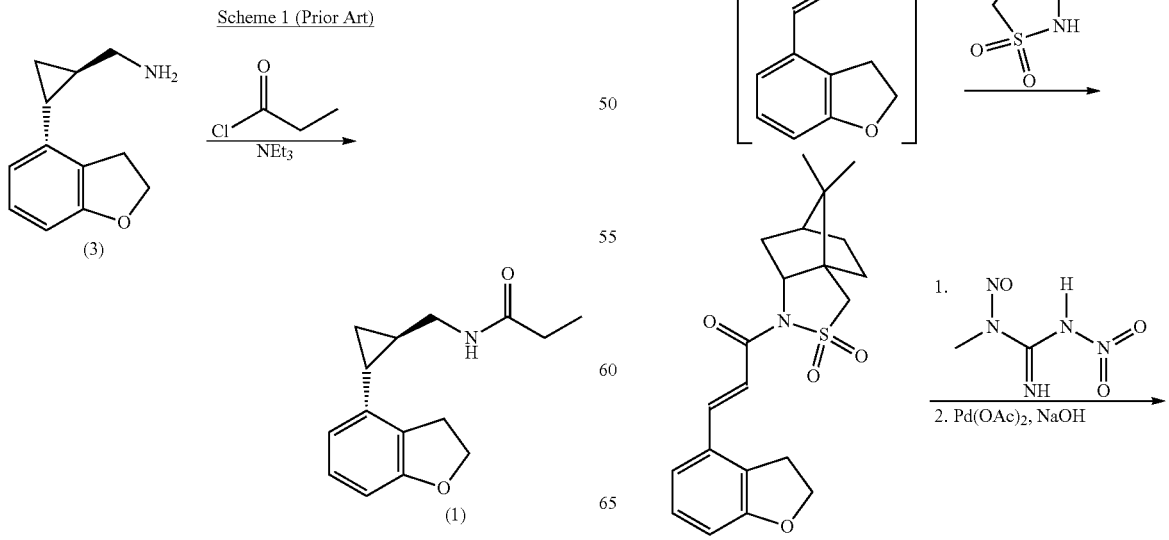

3
-continued

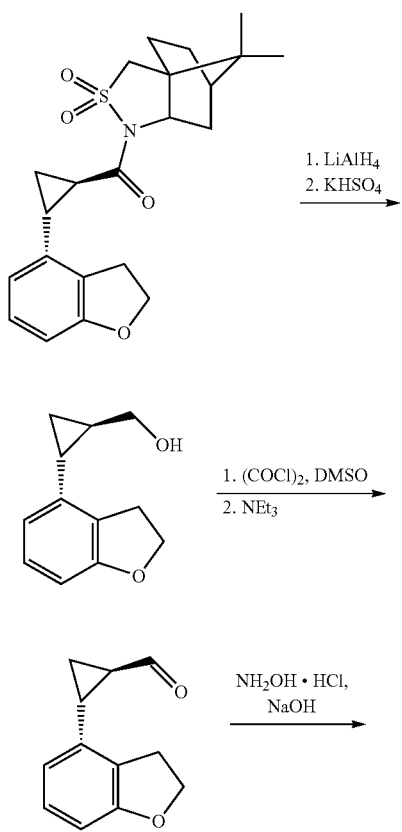

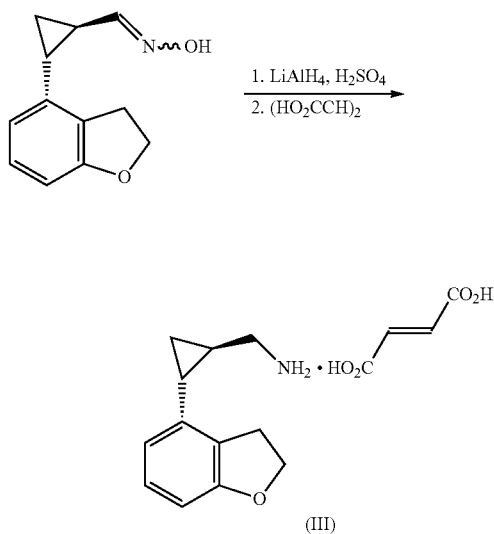

Prasad, J. S et al. in *Org. Process. Res. Dev.* 2003, 7, 821, discloses two approaches for the preparation of epoxide (V), which can be used as an intermediate in the preparation of carboxylic acid (VII) (see Scheme 3). In both approaches, chiral epoxide (V) is prepared from olefin (X), either by Jacobsen asymmetric epoxidation (AE) or a Sharpless asymmetric dihydroxylation (AD) and epoxidation of intermediate diol (IV). If required, chiral enrichment of the intermediates is performed using acid (VII).

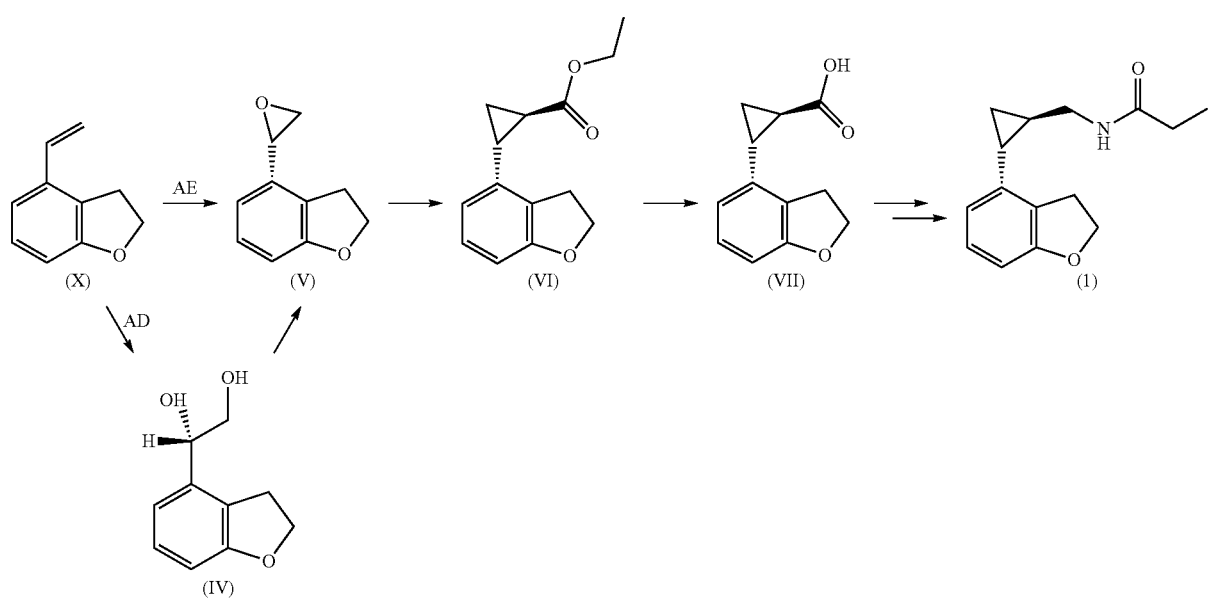

Scheme 3 (Prior Art)

The optimized AE process in Prasad et al. is reported to yield epoxide (V) with 70-74% ee, which was further enriched to >99% ee by crystallization of a (+)-dehydroabietylamine (DAA) salt of the downstream acid (VII). The optimized AD process in Prasad et al. is reported to produce 99% of the desired enantiomer of epoxide (V). Cyclopropanation of epoxide (V) obtained by the AD and AE processes was converted sequentially to ester (VI), acid (VII) and, in several additional downstream steps, Tasimelteon (1) in 22% (AE) and 43% (AD) overall yields from olefin (X).

CN 102675268 A discloses a further process for the preparation of Tasimelteon starting from chiral carboxylic acid (VII), as depicted in Scheme 4. In this process, carboxylic acid (VII) is activated with thionyl chloride before being converted to an amide, which is then reduced and coupled with propionyl chloride to yield Tasimelteon.

stereoselective cyclopropanation of olefin (X) using chiral ruthenium catalysts comprising salen (2,2'-ethylenebis(nitrilomethylidene)diphenol or N, W-ethylenebis(salicylimine)) and alkenyl ligands. In this procedure, carboxylic acid (VII) is produced having 83.6% ee. The Singh publication provides an alternative process involving reaction of chiral epoxide (V) with the anion of triethyl phosphonoacetate (TEPA) to form carboxylic acid (VII). Chiral epoxide (V) is prepared by the AD method reported above, which is capable of producing 99% of the desired enantiomer.

CN 104327022 A discloses a resolution of racemic acid (VIIa) using (R)-1-(α-amino-benzyl)-2-naphthol through the formation of diastereomeric amides, as described in Scheme 5. After resolution of the diastereomeric amides, the desired amide is cleaved to provide carboxylic acid (VII). Carboxylic acid (VII) is then activated, converted to an amide, reduced with borane, and coupled with propionyl chloride to produce Tasimelteon.

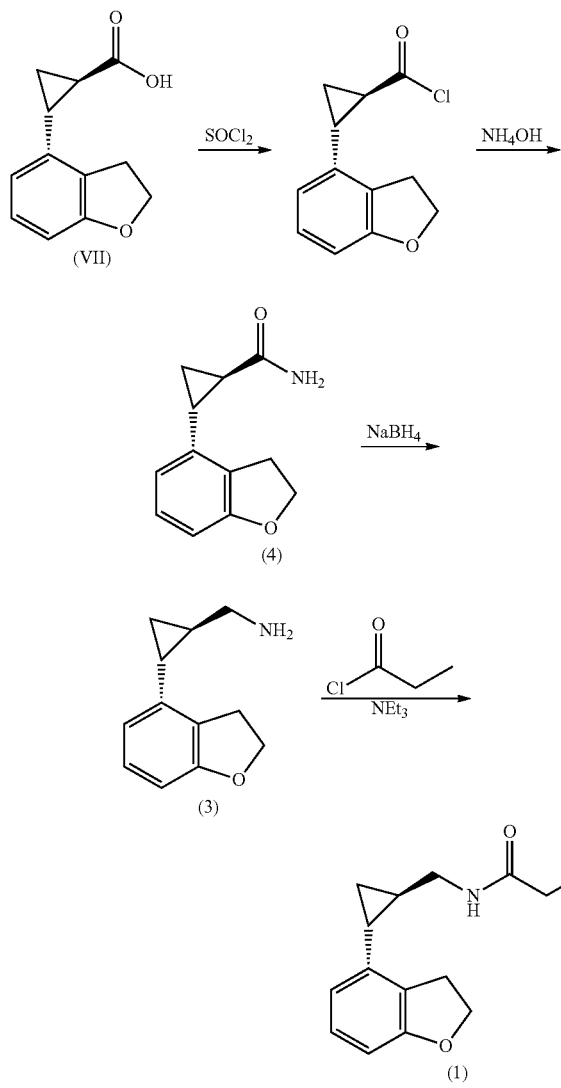

Scheme 4 (Prior Art)

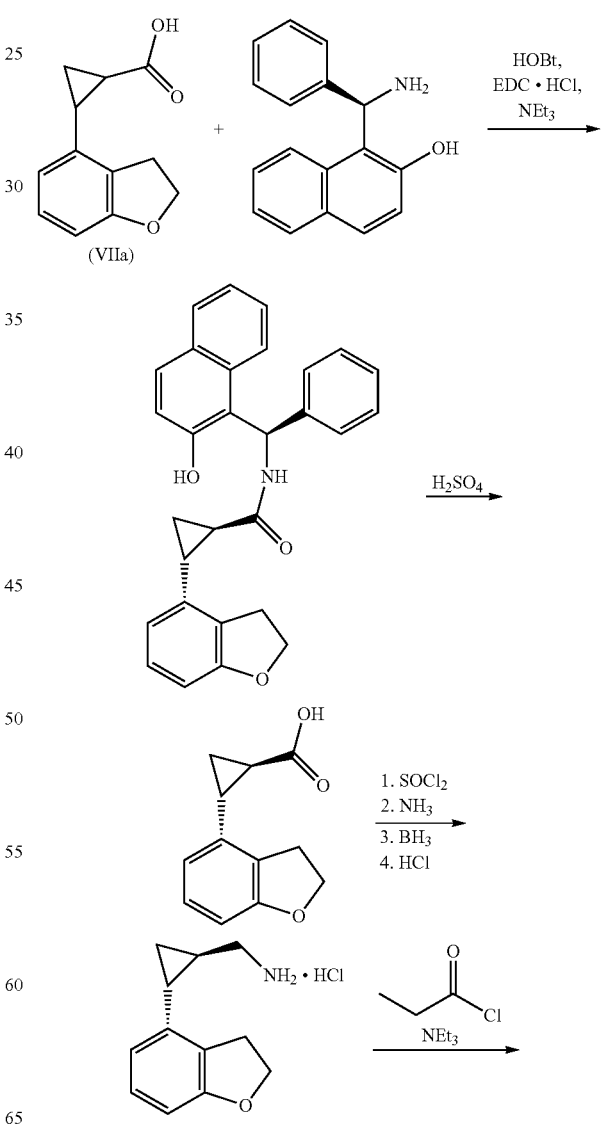

Scheme 5 (Prior Art)

Carboxylic acid (VII) is prepared according to the procedures reported in US 2007/0270593 A1 and Singh, K. A. et al. (Org. Process Res. Dev. 2002, 6, 618). The preparation of acid (VII) reported in US 2007/0270593 A1 involves

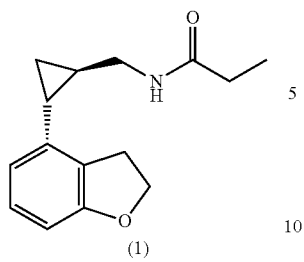

WO 2015/123389 A1 discloses a process for the preparation of Tasimelteon involving an asymmetric cyclopropanation of olefin (X) with ethyl diazoacetate in the presence of a chiral catalyst, as depicted in Scheme 6. Following hydrolysis of the resulting ester to provide carboxylic acid (VII), the chiral purity of carboxylic acid (VII) is enhanced through the formation of a salt with (+)-dehydrobietylamine (DAA). After hydrolysis of the salt, the enantiomerically enriched carboxylic acid (VII) is converted to Tasimelteon through the methods described above.

Scheme 6 (Prior Art)

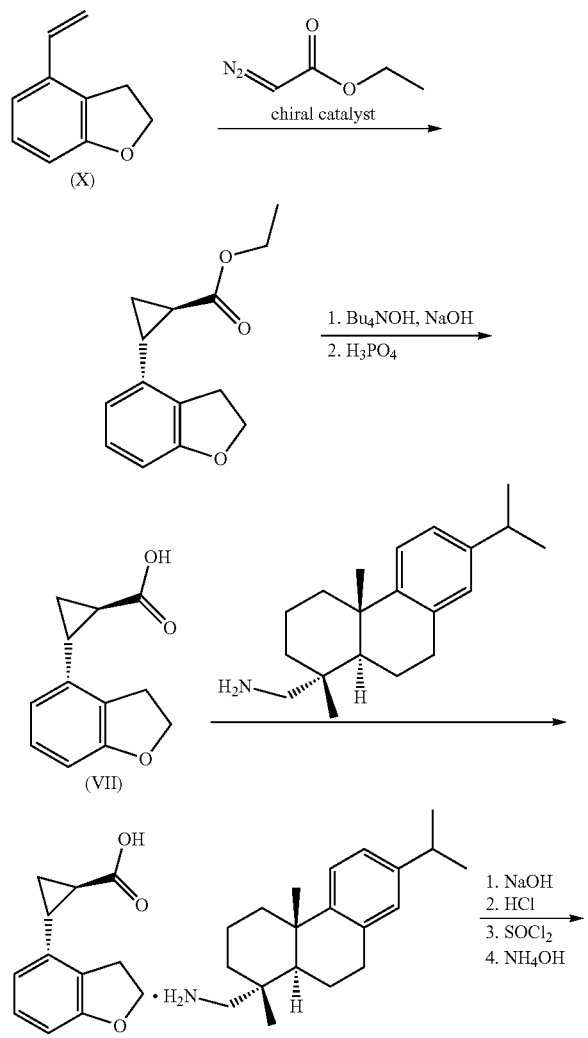

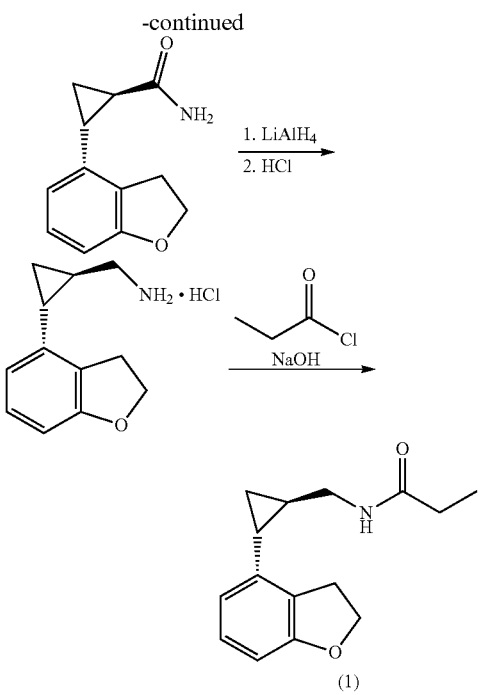

Each of the above processes for the preparation of Tasimelteon suffers from the use of toxic and/or sensitive reagents often requiring specialized handling techniques such as thionyl chloride, borane and lithium aluminum hydride. As a result, it is desired to avoid the use of these reagents during commercial scale manufacturing of pharmaceuticals. Furthermore, in the above processes, chiral enrichment is often obtained through the resolution of carboxylic acid (VII) with a chiral amine, necessitating hydrolysis of the corresponding ester, formation and purification of the salt, hydrolysis of the acid, and re-activation of the acid for the subsequent coupling steps. Alternatively, resolution is obtained through the formation of diastereomeric amides of carboxylic acid (VII), which are then hydrolyzed to reform carboxylic acid (VII).

Owing to the length and complexity of the existing processes for the preparation of Tasimelteon, there remains a need for improved processes for the preparation of Tasimelteon and the intermediates used in such preparations.

SUMMARY

The present invention provides processes for the preparation of Tasimelteon as well as processes for the preparation of intermediates useful in the preparation of Tasimelteon, as depicted in Scheme 7. The processes described herein provide an improved method for the preparation of Tasimelteon wherein the amide of Formula (4) can be prepared directly from the ester of Formula (5) in a single step, thereby eliminating the need to prepare carboxylic acid (VII) as in known processes. A further improvement to the process is provided in the reduction of the amide of Formula (4) to the amine of Formula (3) by using a NaBH$_4$/AlCl$_3$ system with diglyme as the solvent, which aids the solubility of both reagents and raw materials. Use of this reducing system provides safety advantages when compared to lithium- and borane-based systems used in the art, and cost advantages when performed on a commercial scale. If desired, the purity of the amine of Formula (3) can be enhanced by formation and isolation of a salt of Formula (2), which is prepared using a chiral acid as a chiral auxiliary. Following hydrolysis of a salt of Formula (2), propionation of the amine of Formula (3) provides Tasimelteon (1).

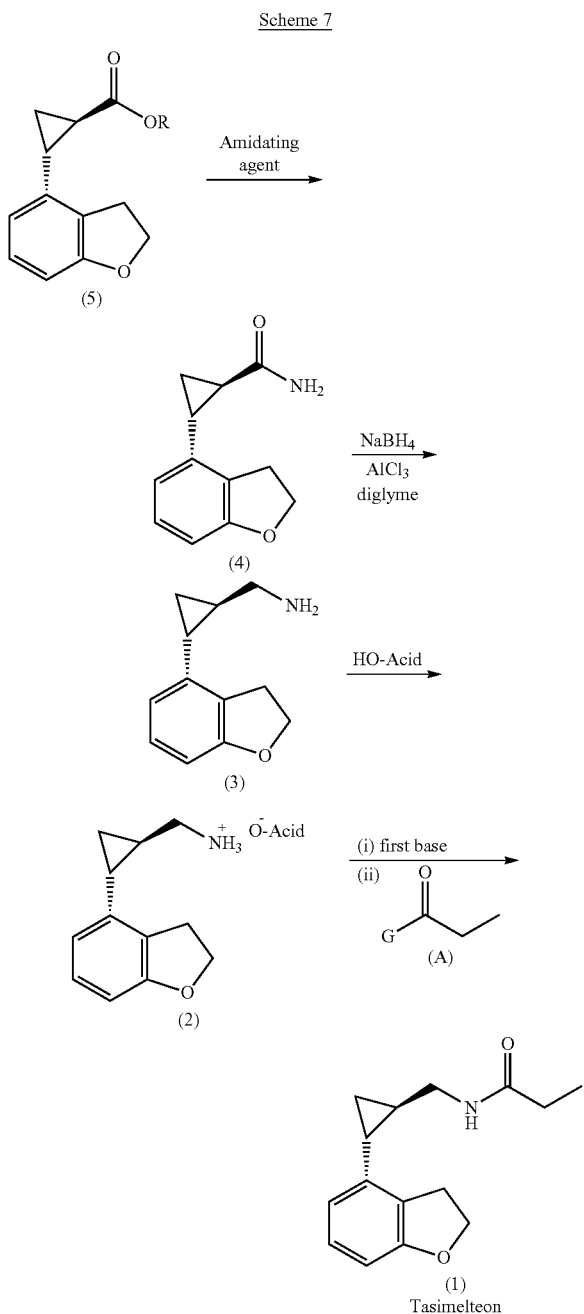

R = C$_1$—C$_4$ alkyl
G = Leaving group
HO-Acid = Optically pure acid

Accordingly, in a first aspect of the present invention, there is provided a process for the preparation of a compound of Formula (4), the process comprising reacting a compound of Formula (5), wherein R is a C$_1$-C$_4$ alkyl chain, preferably ethyl, with either of: (a) methanolic ammonia; or (b) a mixture of formamide and metal alkoxide.

In a first preferred embodiment of the first aspect, the compound of Formula (5) is reacted with methanolic ammonia, optionally in the presence of other solvents. In this embodiment, the reaction with methanolic ammonia may occur in the presence of a metal alkoxide, preferably sodium methoxide. Preferably, the process of the first preferred embodiment is conducted at a temperature of between about 50° C. and about 90° C., more preferably between about 65° C. and about 90° C.

In a second preferred embodiment of the first aspect, the compound of Formula (5) is reacted with a mixture of formamide and metal alkoxide. Preferably, the metal alkoxide is sodium methoxide. Preferably, the process of the second preferred embodiment is conducted at a temperature of between about 20° C. and about 80° C., more preferably between about 20° C. and about 25° C.

In a second aspect of the present invention, there is provided a process for the preparation of a compound of Formula (3) or a salt thereof, the process comprising reducing a compound of Formula (4) with sodium borohydride in the presence of aluminum trichloride and diglyme.

In preferred embodiments of the second aspect, the solvent is a mixture of diglyme with a co-solvent. Preferably, the co-solvent is tetrahydrofuran. Preferably, the process of the second aspect is conducted at a temperature of between about 50° C. and about 90° C., more preferably between about 75° C. and about 85° C. When the compound of Formula (3) is isolated as a salt, the salt is preferably the hydrochloride salt.

In a third aspect of the present invention, there is provided a process for purifying a compound of Formula (3), the process comprising the steps of:

(i) reacting a compound of Formula (3) with (S)-(+)-camphorsulfonic acid in a suitable solvent;

(ii) isolating a salt of Formula (2-A) formed between the compound of Formula (3) and (S)-(+)-camphorsulfonic acid; and (iii) hydrolyzing the salt of Formula (2-A) using a base to obtain the compound of Formula (3);

wherein the purity of the compound of Formula (3) obtained in step (iii) is greater than the purity of the compound of Formula (3) used in step (i). The enhancement of purity in the process of the third aspect may be in respect of chemical or chiral purity.

In preferred embodiments of the third aspect, the solvent comprises toluene or a mixture of toluene and a second solvent. Preferably, the second solvent is selected from the group consisting of diglyme, 2-propanol and methanol. In the process of the third aspect, the base used in step (iii) is preferably an inorganic base, most preferably sodium hydroxide. Preferably, step (iii) conducted in a mixture of water and a water-immiscible solvent; most preferably the water-immiscible solvent is toluene.

If desired, the salt of Formula (2-A) obtained in step (ii) of the third aspect may be further purified prior to step (iii). In a preferred embodiment, the salt of Formula (2-A) is purified by stirring a slurry of the salt of Formula (2-A) in a suitable solvent or mixture of solvents prior to isolating the salt of Formula (2-A) by filtration. Preferably, the solvent comprises a C$_1$-C$_3$ alcohol, preferably methanol or isopropanol. More preferably, the solvent comprises a mixture of toluene and the C$_1$-C$_3$ alcohol.

In a fourth aspect of the present invention, there is provided a salt of Formula (2-A).

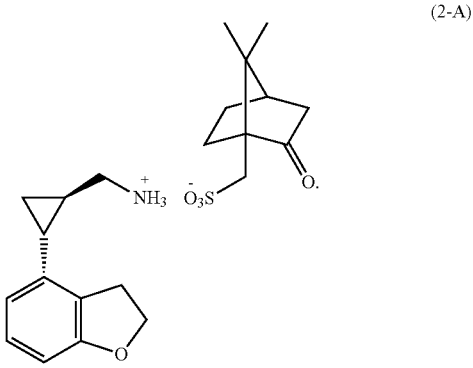

(2-A)

In a fifth aspect of the present invention, there is provided a process for preparing a salt of Formula (2-A), the process comprising the steps of:
(i) reacting a compound of Formula (3) with (S)-(+)-camphorsulfonic acid in a suitable solvent; and
(ii) isolating a salt of Formula (2-A) formed between the compound of Formula (3) and (S)-(+)-camphorsulfonic acid.

In a preferred embodiment of the fifth aspect, the solvent comprises toluene or a mixture of toluene and a second solvent. Preferably, the second solvent is selected from the group consisting of diglyme, 2-propanol and methanol.

In a sixth aspect of the present invention, there is provided a process for preparing a compound of Formula (1), the process comprising:
(i) converting a compound of Formula (5), wherein R is a $C_1$-$C_4$ alkyl chain, to a compound of Formula (4) according to the first aspect of the invention; and
(ii) converting the compound of Formula (4) to the compound of Formula (1).

In a preferred embodiment of the sixth aspect, step (ii) comprises:
(a) converting the compound of Formula (4) to a compound of Formula (3) according to the second aspect of the present invention; and
(b) converting the compound of Formula (3) to the compound of Formula (1).

Preferably, in this preferred embodiment of the sixth aspect, the compound of Formula (3) prepared in step (a) is purified according to the process of third aspect of the present invention prior to converting the compound of Formula (3) to the compound of Formula (1).

In a preferred process for converting the compound of Formula (3) to the compound of Formula (1) in the sixth aspect of the invention, the compound of Formula (3) is converted to the compound of Formula (1) by reacting the compound of Formula (3) with a compound of Formula (A),

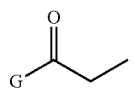

(A)

wherein G is a leaving group. Preferably, the reaction of the compound of Formula (3) with the compound of Formula (A) occurs in the presence of a base, preferably a tertiary amine or metal hydroxide. When the base is an inorganic base, it is preferably sodium hydroxide. When the base is a tertiary amine, it is preferably triethylamine or diisopropylamine. In this process, G of the compound of Formula (A) is preferably a halide, preferably chloride. Alternatively, G of the compound of Formula (A) is propanoate, and the compound of Formula (A) is propionic anhydride.

In a seventh aspect of the present invention, there is provided a process for preparing a compound of Formula (1), the process comprising:
(i) reacting a compound of Formula (3) with (S)-(+)-camphorsulfonic acid in a suitable solvent to form a salt of Formula (2-A);
(ii) isolating the salt of Formula (2-A) formed in step (i);
(iii) treating the salt of Formula (2-A) with a first base to produce a compound of Formula (3), wherein the purity of the compound of Formula (3) formed in step (iii) is greater than the purity of the compound of Formula (3) used in step (i); and
(iv) reacting the compound of Formula (3) prepared in step (iii) with a compound of Formula (A) wherein G of the compound of Formula (A) is a leaving group.

The enhancement of purity in step (iii) of the process of the seventh aspect may be in respect of chemical or chiral purity.

In preferred embodiments of the seventh aspect, the solvent comprises toluene or a mixture of toluene and a second solvent. Preferably, the second solvent is selected from the group consisting of diglyme, 2-propanol and methanol. In the process of the seventh aspect, the first base used in step (iii) is preferably an inorganic base, most preferably sodium hydroxide. Preferably, step (iii) conducted in a mixture of water and a water-immiscible solvent; most preferably the water-immiscible solvent is toluene.

If desired, the salt of Formula (2-A) obtained in step (ii) of the seventh aspect may be further purified prior to step (iii). In a preferred embodiment, the salt of Formula (2-A) is purified by stirring a slurry of the salt of Formula (2-A) in a suitable solvent or mixture of solvents prior to isolating the salt of Formula (2-A) by filtration. Preferably, the solvent comprises a $C_1$-$C_3$ alcohol, preferably methanol or isopropanol. More preferably, the solvent comprises a mixture of toluene and the $C_1$-$C_3$ alcohol.

In a preferred embodiment of step (iv) of the seventh aspect, the reaction of the compound of Formula (3) with the compound of Formula (A) occurs in the presence of a second base, preferably a tertiary amine or metal hydroxide. Optionally, the second base may be the same as the first base. When the second base is a tertiary amine, it is preferably triethylamine or diisopropylamine. When the base is an inorganic base, it is preferably sodium hydroxide. In this process, G of the compound of Formula (A) is preferably a halide, preferably chloride. Alternatively, the compound of Formula (A) is propionic anhydride.

In further preferred embodiments of the seventh aspect, the compound of Formula (3) is prepared according to the second aspect of the present invention. In a still further preferred embodiment of the seventh aspect, the compound of Formula (3) used in step (i) is prepared by:
(i) converting a compound of Formula (5), wherein R is a $C_1$-$C_4$ alkyl chain, to a compound of Formula (4) according to the process of the first aspect of the invention; and
(ii) converting the compound of Formula (4) to the compound of Formula (3) according to the process of the second aspect of the invention.

In an eighth aspect of the present invention, there is provided a process for the preparation of a compound of Formula (1), the process comprising the steps of:

(i) reacting a compound of Formula (5), wherein R is a C$_1$-C$_4$ alkyl chain, with either of: (a) methanolic ammonia; or (b) a mixture of formamide and metal alkoxide, to form a compound of Formula (4);

(ii) reducing the compound of Formula (4) with sodium borohydride in the presence of aluminum trichloride using diglyme as a solvent to form a compound of Formula (3);

(iii) purifying the compound of Formula (3) by formation of a salt of Formula (2-A) prepared by reacting a compound of Formula (3) with (S)-(+)-camphorsulfonic acid;

(iv) treating the salt of Formula (2-A) with a first base to produce a compound of Formula (3), wherein the purity of the compound of Formula (3) produced is greater than the purity of the compound of Formula (3) formed in step (ii); and (v) reacting the compound of Formula (3) prepared in step (iv) with a second base and a compound of Formula (A), wherein G in the compound of Formula (A) is a leaving group.

DETAILED DESCRIPTION

The present invention provides processes for the preparation of Tasimelteon, as well as processes for the preparation of intermediates useful in the preparation of Tasimelteon. Through the use of these processes, the preparation of Tasimelteon avoids the need of preparing carboxylic acid (VII) as an intermediate. Further, when practiced according to the preferred embodiments described herein, the processes of the invention also have the advantage that these steps can be conducted in good yield using comparatively mild conditions when compared to those used in the art, which can translate to cost savings and safety advantages when performed at an industrial scale.

As used herein, the term "alkyl" means, unless otherwise stated, a straight or branched chain, saturated hydrocarbon group having the number of carbon atoms designated (e.g., C$_1$-C$_4$ means one to four carbon atoms). Examples of saturated hydrocarbon groups include methyl, ethyl, n-propyl, isopropyl, n-butyl, t-butyl, isobutyl and sec-butyl.

As used herein, wt % refers to weight percent and is used to express weight solute/weight solution as a percentage.

As used herein, the term "volumes" refers to the parts of solvent or liquids by volume (mL) with respect to the weight of solute (g). For example, when a reaction is conducted using 1 g of starting material and 100 mL of solvent, it is said that 100 volumes of solvent are used.

As used herein, "room temperature" generally refers to a temperature of 20-25° C.

As used herein, the term "about" means "close to" and that variation from the exact value that follows the term are within amounts that a person of skill in the art would understand to be reasonable. For example, when the term "about" is used with respect to temperature, a variation of ±5° C. is generally acceptable when carrying out the processes of the present invention; when used with respect to mole equivalents, a variation of ±0.1 moles is generally acceptable; and when used with respect to volumes, a variation of 10% is generally acceptable.

As used herein, the (1R,2R)-isomer is shown as the major component of the compounds of Formulas (1), (3), (4) and (5). Other stereoisomers (e.g., the (1S,2S)-isomer) and impurities may be present as minor components. It will be appreciated by a skilled person that, where relative amounts of reagents are indicated, such amounts are not corrected for chemical or chiral/optical purity.

In one embodiment of the present invention, a process is provided for the preparation of a compound of Formula (4):

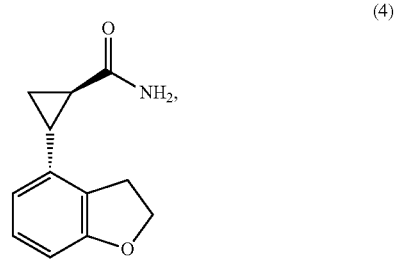

the process comprising reacting a compound of Formula (5):

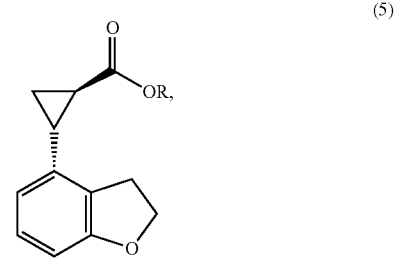

wherein R is a C$_1$-C$_4$ alkyl chain,
with either:
a) methanolic ammonia; or
b) a mixture of formamide and metal alkoxide.

In the compound of Formula (5), R may be selected from the group consisting of methyl, ethyl, n-propyl, isopropyl, n-butyl, t-butyl, isobutyl and sec-butyl. Preferably, R is ethyl.

Optionally, the methanolic ammonia is mixed with a solvent. When the methanolic ammonia is mixed with a solvent, this solvent is preferably a C$_2$-C$_4$ alcohol.

In the reaction of a compound of Formula (5) with methanolic ammonia to produce a compound of Formula (4), a metal alkoxide may be used. The metal alkoxide may be an alkali metal alkoxide or an alkaline earth metal alkoxide. Suitable alkali metals include lithium, potassium and sodium. Suitable alkaline earth metals include magnesium and calcium. Suitable alkoxide anions include methoxide, ethoxide, propoxide, isopropoxide, butoxide, sec-butoxide and tert-butoxide. A preferred metal alkoxide is sodium methoxide. The metal alkoxide is preferably provided as a solution in the corresponding alcohol solvent, most particularly sodium methoxide in methanol. The amount of metal alkoxide used may vary from a catalytic amount to one or more mole equivalents with respect to the compound of Formula (5). Preferably a catalytic amount of the metal alkoxide is used.

The reaction of a compound of Formula (5) with methanolic ammonia may be conducted at any suitable temperature. Preferably, the temperature is in the range of about 50° C. to about 90° C., more preferably between about 65 and about 75° C. To facilitate completion of the reaction, the reaction of a compound of Formula (5) with methanolic ammonia is preferably conducted in a pressure sealed vessel.

In the reaction of a compound of Formula (5) with a mixture of formamide and metal alkoxide to produce a compound of Formula (4), the amount of formamide used may be from at least about 1 mole equivalent with respect to the compound of Formula (5). If desired, formamide may be used as the solvent for the reaction. When used as a solvent, a sufficient amount of formamide is used to facilitate stirring. A preferred amount of formamide expressed in volumes with respect to the weight of a compound of Formula (5) is from about 3 volumes to about 5 volumes.

In the reaction of a compound of Formula (5) with a mixture of formamide and metal alkoxide to produce a compound of Formula (4), the metal alkoxide may be an alkali metal alkoxide or an alkaline earth metal alkoxide. Suitable alkali metals include lithium, potassium and sodium. Suitable alkaline earth metals include magnesium and calcium. Suitable alkoxide anions include methoxide, ethoxide, propoxide, isopropoxide, butoxide, sec-butoxide and tert-butoxide. A preferred metal alkoxide is sodium methoxide. The metal alkoxide is preferably provided as a solution in the corresponding alcohol solvent, particularly sodium methoxide in methanol. The mole equivalents of metal alkoxide with respect to the compound of Formula (5) may vary from about 1 mole equivalent, and is preferably from about 2 to about 3 mole equivalents.

The reaction of a compound of Formula (5) with a mixture of formamide and metal alkoxide to produce a compound of Formula (4) may be conducted in the presence of a suitable solvent. Suitable solvents include hydrocarbon solvents such as toluene, chlorinated solvents such as dichloromethane, ether solvents such as tetrahydrofuran, and polar, aprotic solvents such as dimethylformamide. Preferably, the reaction is conducted with formamide acting as both reagent and solvent.

The reaction of a compound of Formula (5) with a mixture of formamide and metal alkoxide may be conducted at any suitable temperature. Preferably, the reaction temperature is in the range of about 20° C. to about 80° C. However, the reaction may conveniently be conducted at a temperature of about 20° C. to about 25° C.

In a second embodiment of the present invention, there is provided a process for the preparation of Tasimelteon, the process comprising:
  (i) converting a compound of the Formula (5) to a compound of Formula (4) according to the first embodiment of the present invention; and
  (ii) converting the compound of Formula (4) to Tasimelteon.

Conversion of the compound of Formula (4) to Tasimelteon in step (ii) may be performed according to known procedures reported in the art, for example as reported in the documents cited herein, or according to the further embodiments of the present invention described below.

In a third embodiment of the present invention, there is provided a process for the preparation of a compound of Formula (3):

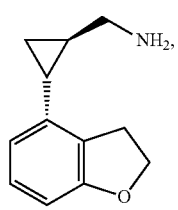

(3)

the process comprising reducing a compound of Formula (4) with sodium borohydride in the presence of aluminium trichloride and diglyme to produce the compound of Formula (3), or a salt thereof.

In the reduction of the compound of Formula (4) with sodium borohydride, the mole equivalents of sodium borohydride with respect to a compound of Formula (4) is generally at least about 1.5 mole equivalents, preferably about 2 mole equivalents. The mole equivalents of aluminum trichloride with respect to a compound of Formula (4) is preferably from at least about 0.9 mole equivalents, preferably about 1.2 mole equivalents.

The reduction of the compound of Formula (4) with sodium borohydride is conducted in the presence of a solvent comprising diglyme. The amount of diglyme is preferably sufficient to promote dissolution of the reagents, particularly the borohydride. Preferably, the amount of diglyme used is in the range of from about 6 volumes to about 10 volumes with respect to the compound of Formula (4). It has been found that higher amounts of diglyme typically correspond with more extensive work-up procedures, including water washes. The diglyme may also be used in combination with other solvents, such as tetrahydrofuran.

The reaction of a compound of Formula (4) with sodium borohydride may be conducted at any suitable temperature. Preferably, the temperature is in the range of about 50° C. to about 90° C. Most preferably, the reaction is conducted at about 75° C. to about 85° C. At higher temperatures (above 90° C.), it has been found that sodium borohydride is susceptible to crystallization, which may slow the reaction.

The compound of Formula (3) may be isolated as the free base or a salt form thereof having Formula (3').

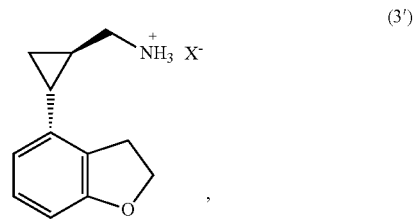

(3')

wherein X⁻ is the counter-ion of the acid (HX) used to form the salt.

Any suitable salt of Formula (3') may be formed to allow for ease of isolation and handling of the intermediate. A preferred salt of Formula (3') is the hydrochloride salt of Formula (3-A) formed between the compound of Formula (3) and hydrochloric acid.

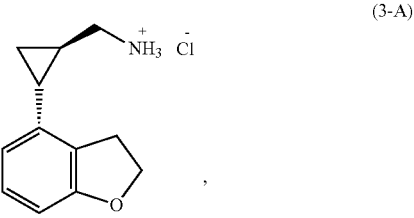

(3-A)

Alternatively, the compound of Formula (3) is not required to be isolated, and may be used directly in the further preparation of Tasimelteon. If desired, the compound of Formula (3) can be purified to increase its chemical or chiral purity according to the sixth embodiment of the present invention described below.

In a fourth embodiment of the present invention, there is provided a process for the preparation of Tasimelteon, the process comprising:
(i) preparing the compound of Formula (3) from the compound of Formula (4) according to the third embodiment of the present invention; and
(ii) converting the compound of Formula (3) to Tasimelteon.

Conversion of the compound of Formula (3) to Tasimelteon in step (ii) may be performed according to known procedures reported in the art, for example as reported in the documents cited herein, or according to the further embodiments of the present invention described below.

In a fifth embodiment of the present invention, there is provided a process for the preparation of Tasimelteon, the process comprising:
(i) preparing the compound of Formula (4) from the compound of Formula (5) according to the first embodiment of the present invention;
(ii) preparing the compound of Formula (3) from the compound of Formula (4) according to the third embodiment of the present invention; and
(iii) converting the compound of Formula (3) to Tasimelteon.

Conversion of the compound of Formula (3) to Tasimelteon in step (iii) may be performed according to known procedures reported in the art, for example as reported in the documents cited herein, or according to the further embodiments of the present invention described below.

In a sixth embodiment of the present invention, there is provided a process for purifying the compound of Formula (3), the process comprising:
(i) reacting a compound of Formula (3)

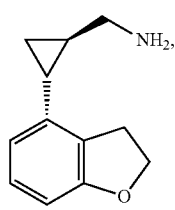

(3)

with (S)-(+)-camphorsulfonic acid in a suitable solvent;
(ii) isolating a salt of Formula (2-A) formed between the compound of Formula (3) and (S)-(+)-camphorsulfonic acid; and
(iii) hydrolyzing the salt of Formula (2-A) using a base to obtain the compound of Formula (3);
wherein the purity of the compound of Formula (3) obtained in step (iii) is greater than the purity of the compound of Formula (3) used in step (i).

In step (i) of the sixth embodiment, the compound of Formula (3) has an initial chemical and chiral purity. The initial chiral purity is generally enriched in the (1R, 2R)-isomer following the preparation of the compound of Formula (5) by processes known in the art, including those discussed above. Preferably, the initial chiral purity is greater than about 85%. Most preferably, the initial chiral purity is greater than 95% (i.e., 95 (1R,2R): 5 (1 S,2S)).

Optionally, the sixth embodiment of the present invention can be carried out using a salt of the compound of Formula (3) having Formula (3'). Preferably, the salt of Formula (3'), is the hydrochloride salt. When using a salt of Formula (3'), the salt is first hydrolyzed using a base to provide the compound of Formula (3), following which the salt of Formula (2-A) is prepared from the compound of Formula (3). Preferably, when hydrolyzing the salt of Formula (3'), sodium hydroxide is used as the base, and the hydrolysis is conducted in a mixture of toluene and water.

The salt of Formula (2-A) is a crystalline solid providing for ease of isolation compared to the free amine of Formula (3), which exists as an oil.

In the reaction of a compound of Formula (3) with (S)-(+)-camphorsulfonic acid, an approximately equimolar amount of (S)-(+)-camphorsulfonic acid with respect to the amount of the compound of Formula (3) is preferably used.

The reaction of a compound of Formula (3) with (S)-(+)-camphorsulfonic acid is conducted in the presence of a suitable solvent. Preferred solvents comprise toluene, and particularly mixtures of toluene and other solvents, including toluene and diglyme, toluene and 2-propanol, or toluene and methanol.

Isolation of a salt of Formula (2-A) involves standard techniques known to a skilled person, such as filtration. Preferably, isolation provides removal of the salt of Formula (2-A) from associated stereoisomers and/or other related chemical impurities.

If desired, the chiral and/or chemical purity of the salt of Formula (2-A) may be further enriched by one or more purification steps following step (ii). Purification is preferably accomplished by preparation of a slurry of the salt of Formula (2-A) in a suitable solvent or mixture of solvents, and stirring the slurry for a period of time prior to isolation of the purified salts by filtration.

Suitable solvents for the purification of the salt of Formula (2-A) comprises a $C_1$-$C_3$ alcohol, particularly 2-propanol. Other preferred solvents for the purification of the salt of Formula (2-A) include mixtures of toluene and a $C_1$-$C_3$ alcohol solvent, including mixtures of toluene with 2-propanol and toluene with methanol.

When purifying the salt of Formula (2-A), the slurry may be heated and maintained at an elevated temperature for a suitable time prior to isolation by filtration. For example, the slurry may be heated to a temperature in the range of about 50° C. and about 75° C. Maintaining the slurry at the elevated temperature for about 6 hours is generally suitable for facilitating the purification of the salt of Formula (2-A) and providing a more uniform particle size. However, shorter or longer times may also be used depending on the processing conditions selected and the desired level of purity.

Alternatively, the salt of Formula (2-A) can be purified by recrystallization from a suitable solvent system, such as methanol or butanol.

The first base used in step (iii) may be any suitable organic or inorganic base. Examples of suitable bases include tertiary amines such as triethylamine and diisopropylethylamine and metal hydroxides such as sodium hydroxide.

Step (iii) is conveniently conducted in a suitable solvent. Suitable solvents are those that are considered to be compatible with the reaction including, for example, strongly basic conditions. When an inorganic base such as sodium hydroxide is used, the solvent preferably comprises both water and a water-immiscible solvent. Suitable water-immiscible solvents include ethers such as methyl t-butyl ether and aromatic hydrocarbons such as toluene. When an organic base is used, water-miscible solvents may also be used. Preferably, the solvent is a mixture of toluene and water.

The compound of Formula (3) formed following hydrolysis of the salt of Formula (2-A) may be separated from the (S)-(+)-camphorsulfonic acid that was used as a chiral auxiliary, or it may be used in the subsequent reaction with the compound of Formula (A) without separation from the (S)-(+)-camphorsulfonic acid. When the compound of Formula (3) and the (S)-(+)-camphorsulfonic acid are separated, the (S)-(+)-camphorsulfonic acid may be recycled for use in subsequent reactions.

In a seventh embodiment of the present invention, there is provided a process for the preparation of Tasimelteon, the process comprising:
(i) preparing the compound of Formula (3) from the compound of Formula (4) according to the third embodiment of the present invention;
(ii) purifying the compound of Formula (3) according to the sixth embodiment of the present invention; and
(iii) converting the compound of Formula (3) to Tasimelteon.

Conversion of the compound of Formula (3) to Tasimelteon in step (iii) may be performed according to known procedures reported in the art, for example as reported in the documents cited herein, or according to the further embodiments of the present invention described below.

Alternatively, according to the seventh embodiment of the present invention, there is provided a process for the preparation of Tasimelteon, the process comprising:
(i) preparing the compound of Formula (3) from the compound of Formula (4) according to the third embodiment of the present invention;
(ii) purifying the compound of Formula (3) by preparing a salt of Formula (2-A) according to the sixth embodiment of the present invention; and
(iii) converting the salt of Formula (2-A) to Tasimelteon without first isolating the compound of Formula (3) following hydrolysis the salt of Formula (2-A) with base.

Conversion of the salt of Formula (2-A) to Tasimelteon in step (iii) may be performed according to known procedures reported in the art, for example as reported in the documents cited herein, or according to the further embodiments of the present invention described below.

In an eighth embodiment of the present invention, there is provided a process for the preparation of a salt of Formula (2-A), the process comprising:
(i) preparing a compound of Formula (4) from the compound of Formula (5) according to the first embodiment of the present invention;
(ii) preparing a compound of Formula (3) from the compound of Formula (4) according to the third embodiment of the present invention; and
(iii) preparing a salt of Formula (2-A) from the compound of Formula (3) according to the sixth embodiment of the present invention.

In a ninth embodiment of the present invention, there is provided a process for the preparation of Tasimelteon, the process comprising:
(i) treating the salt of Formula (2-A) with a first base to produce a compound of Formula (3); and
(ii) reacting, in the presence of a second base, the compound of Formula (3) with a compound of Formula (A):

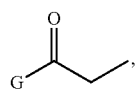

wherein G is a leaving group;
to provide Tasimelteon.

The first base used in step (i) may be any suitable organic or inorganic base. Examples of suitable bases include tertiary amines such as triethylamine and diisopropylethylamine and metal hydroxides such as sodium hydroxide.

Step (i) is conveniently conducted in a suitable solvent. Suitable solvents are those that are considered to be compatible with the reaction including, for example, strongly basic conditions. When an inorganic base such as sodium hydroxide is used, the solvent preferably comprises both water and a water-immiscible solvent. Suitable water-immiscible solvents include ethers such as methyl t-butyl ether and aromatic hydrocarbons such as toluene. When an organic base is used, water-miscible solvents may also be used. Preferably, the solvent is a mixture of toluene and water.

The compound of Formula (3) formed following hydrolysis of the salt of Formula (2-A) may be separated from the (S)-(+)-camphorsulfonic acid that was used as a chiral auxiliary, or it may be used in the subsequent reaction with the compound of Formula (A) without separation from the (S)-(+)-camphorsulfonic acid.

The compound of Formula (A) employed in step (ii) is an activated propionic acid derivative wherein the substituent G is any suitable leaving group. Exemplary compounds of Formula (A) include propionyl halides (for example, G is a halide, preferably chloride) or propionic anhydride (for example, G is propanoate). For suitable yields, the mole equivalents of the compound of Formula (A) with respect to the compound of Formula (3) is preferably between about 1 to about 1.1 mole equivalents. Most preferably, the mole equivalents of the compound of Formula (A) is 1.1.

The second base used in step (ii) may be the same or different from the first base used in step (i). Examples of suitable second bases are the same as those for the first base.

Step (ii) may be conducted in a suitable solvent. Suitable solvents compatible with the reaction are used. When an inorganic base such as sodium hydroxide is used, the solvent preferably comprises both water and a water-immiscible solvent. Suitable water-immiscible solvents may include ethers such as methyl t-butyl ether and aromatic hydrocarbons such as toluene. When an organic base is used, water-miscible solvents may also be used. Solvents may be selected from the group consisting of ethers such as methyl t-butyl ether, aromatic hydrocarbons such as toluene, dialkyamides such as dimethylformamide and chlorinated hydrocarbons such as dichloromethane. Preferably, the solvent is a mixture of toluene and water.

Optionally, steps (i) and (ii) may be conducted in the same solvent wherein the compound of Formula (3) is not isolated, but is used directly in the following reaction of step (ii).

The reaction of the liberated compound of Formula (3) with the compound of Formula (A) may be conducted at a temperature in the range of about 0° C. and about 40° C. Preferably, the reaction is conducted at about 20° C. to about 25° C.

In an alternative to the ninth embodiment of the present invention, there is provided a process for the preparation of Tasimelteon, the process comprising:
(i) purifying a compound of Formula (3) according to the sixth embodiment of the present invention; and
(ii) reacting, in the presence of a base, the compound of Formula (3) with a compound of Formula (A):

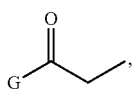

wherein G is a leaving group;
to provide Tasimelteon.

In a tenth embodiment of the present invention, there is provided a process for the preparation of Tasimelteon, the process comprising:

(i) preparing a compound of Formula (4) from the compound of Formula (5) according to the first embodiment of the present invention;

(ii) preparing a compound of Formula (3) from the compound of Formula (4) according to the third embodiment of the present invention; and (iii) preparing a salt of Formula (2-A) or purifying the compound of Formula (3) according to the sixth embodiment of the present invention; and (iv) converting the salt of Formula (2-A) or the purified compound of Formula (3) to Tasimelteon according to the ninth embodiment of the present invention.

In a preferred embodiment of the present invention, Tasimelteon is prepared according to the exemplary process depicted in Scheme 8.

Scheme 8

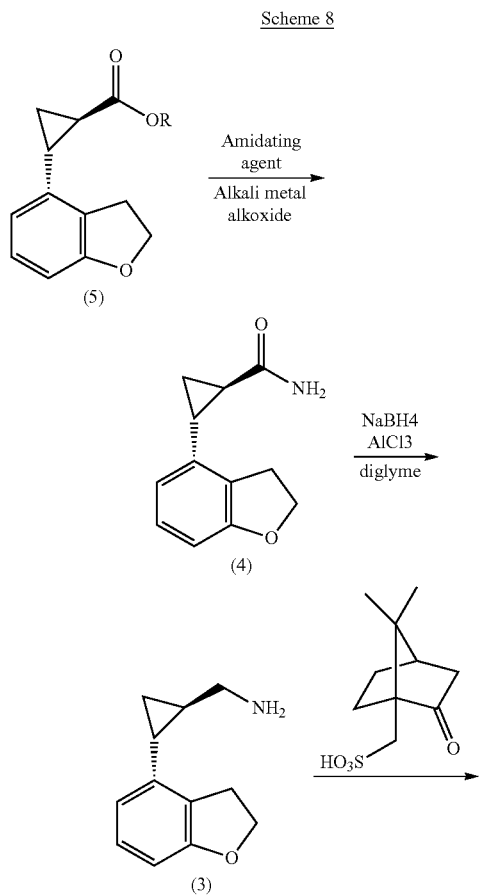

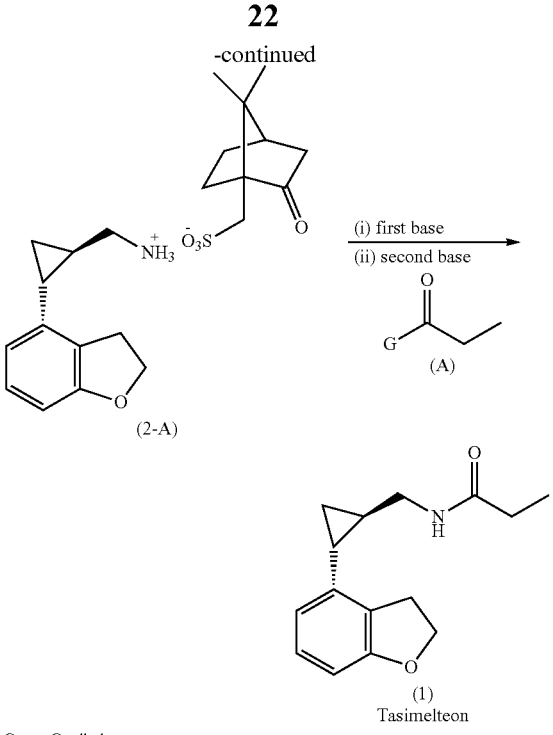

$R = C_1$—$C_4$ alkyl
$G =$ Leaving group

EXAMPLES

The following examples are illustrative of some of the embodiments of the invention described herein. It will be apparent to the skilled reader that various alterations to the described processes in respect of the reactants, reagents and conditions may be made when using the processes of the present invention without departing from the scope or intent thereof.

In Examples 1, 2 and 4 to 7, the compound of Formula (5) was prepared according to the procedure described in Example 3.

Example 1

Preparation of (1R,2R)-2-(2,3-dihydro-1-benzofuran-4-yl)cyclopropane-1-carboxamide (Formula (4))

To a solution of ethyl (1R,2R)-2-(2,3-dihydro-1-benzofuran-4-yl)cyclopropane-1-carboxylate (Formula (5), R=ethyl) (14.3 g, 61.56 mmol) in toluene (8 mL) was added formamide (44 mL) and sodium methoxide (25 wt %) in ethanol (26.5 g, 123.1 mmol) at room temperature. The resulting clear, reddish brown solution changed to a yellowish brown suspension within 15 minutes. The yellowish brown suspension was stirred at room temperature for about 4 hours. Following completion of the reaction (as monitored by Thin Layer Chromatography (TLC)), water (88 mL) was added to the suspension at room temperature, and the mixture was stirred for about 1 hour. The precipitated product was collected by filtration at room temperature, washed with water (2×24 mL), and dried in vacuo at 45-50° C. to afford (1R,2R)-2-(2,3-dihydro-1-benzofuran-4-yl)cyclopropane-1-carboxamide (Formula (4)) (9.2 g, 73% yield) as a beige solid, 98.7% purity by HPLC (area %).

Example 2

Preparation of (1R,2R)-2-(2,3-dihydro-1-benzofuran-4-yl)cyclopropane-1-carboxamide (Formula (4))

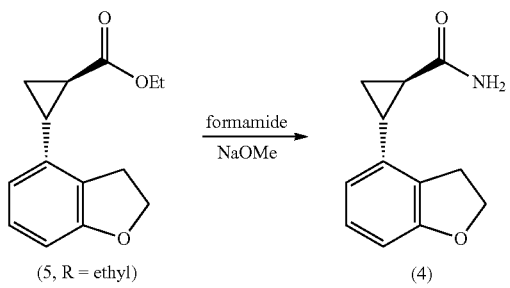

To a solution of ethyl (1R,2R)-2-(2,3-dihydro-1-benzofuran-4-yl)cyclopropane-1-carboxylate (Formula (5), R=ethyl, 67 g, 288.42 mmol) in formamide (335 mL) was added sodium methoxide (25 wt %) in methanol (124.6 g, 576.80 mmol). The clear, brown solution became a light pinkish brown suspension within 15 minutes, and was stirred at room temperature for about 18 hours. Following completion of the reaction (as monitored by TLC), the resulting suspension was cooled to 0-5° C. and water (670 mL) was added over 0.5 hours. The suspension was further stirred at 0-5° C. for about 2 hours. The product was collected by filtration, washed with water (2×120 mL) and ethyl acetate (1×120 mL), and then dried in vacuo at 45-50° C. to afford (1R,2R)-2-(2,3-dihydro-1-benzofuran-4-yl)cyclopropane-1-carboxamide (Formula (4)) (43.7 g, 74.5% yield) as a beige solid, 99.8% purity by HPLC (area %).

Example 3

Preparation of (1R,2R)-2-(2,3-dihydro-1-benzofuran-4-yl)cyclopropane-1-carboxamide (Formula (4))

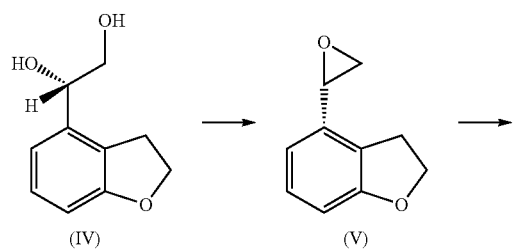

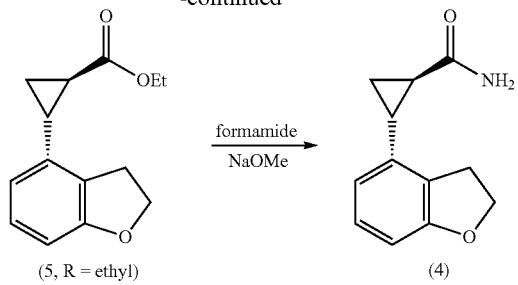

To a solution of (1S)-1-(2,3-dihydro-1-benzofuran-4-yl)ethane-1,2-diol (Formula (IV)) (100 g, 554.9 mmol) in tetrahydrofuran (500 mL) was added trimethyl orthoacetate (121.9 g, 1014.6 mmol), and the mixture was cooled to 0-5° C. To this mixture was added trimethylsilyl chloride (110.1 g, 1013.9 mmol) at 0-5° C., and the mixture was stirred for about 3 hours. Following completion of the reaction, potassium t-butoxide (20 wt %) in tetrahydrofuran (89 g, 793.5 mmol) was added at 0-5° C., and the mixture was maintained for about 2 hours. Following completion of the reaction, water (700 mL) was added and the pH of the mixture was adjusted to 7-7.5. The aqueous and organic phases were separated, and the aqueous phase was extracted with toluene (2×200 mL). The combined organic phases were concentrated in vacuo at 40-45° C. to a volume of 250 mL. To this solution was added toluene (300 mL), and the mixture was again concentrated in vacuo at 40-45° C. to 300 mL to afford a solution of 4-[(2S)-oxiran-2-yl]-2,3-dihydro-1-benzofuran (Formula (V)) in toluene.

In another flask, sodium t-butoxide (106.7 g, 1110 mmol) was suspended in tetrahydrofuran (300 mL) and cooled to about 5° C. before triethyl phosphonoacetate (286.2 g, 1276 mmol) while maintaining the temperature below 30° C. To this mixture was added the previously prepared solution of 4-[(2S)-oxiran-2-yl]-2,3-dihydro-1-benzofuran (Formula (V)) in toluene at room temperature. The mixture was then heated to 70-75° C. and stirred for about 18 hours. Following completion of the reaction, the mixture was cooled to room temperature and water (700 mL) was added. The organic and aqueous phases were separated, and the aqueous phase was extracted with toluene (2×200 mL). The combined organic phases were concentrated in vacuo at 40-45° C. to 250 mL volume to afford ethyl (1R,2R)-2-(2,3-dihydro-1-benzofuran-4-yl)cyclopropane-1-carboxylate (Formula (5), R=ethyl) in toluene.

The temperature of the solution of ethyl (1R,2R)-2-(2,3-dihydro-1-benzofuran-4-yl)cyclopropane-1-carboxylate (Formula (5), R=ethyl) in toluene was adjusted to room temperature and formamide (500 mL) was added. The mixture was heated and concentrated in vacuo at 40-45° C. to 650 mL to ensure toluene was removed from the reaction mixture. Following adjustment to room temperature, sodium methoxide (25 wt %) in methanol (239.7 g, 1109.8 mmol) was added. The clear, brown solution changed to a light, yellowish brown suspension within 15 minutes. The suspension was heated to 45-50° C. and stirred for about 22 hours. Following completion of the reaction, the suspension was cooled to room temperature and water (1000 mL) was added. The suspension was further stirred at room temperature for about 1 hour. The product was collected by filtration, washed with water (2×200 mL) and dried in vacuo at 50-60° C. to afford (1R,2R)-2-(2,3-dihydro-1-benzofuran-4-yl)cyclopropane-1-carboxamide (Formula (4)) (84 g, 74.5% yield from diol) as a beige solid, 99.5% purity by HPLC (area %).

Example 4

Preparation of (1R,2R)-2-(2,3-dihydro-1-benzo-furan-4-yl)cyclopropane-1-carboxamide (Formula (4))

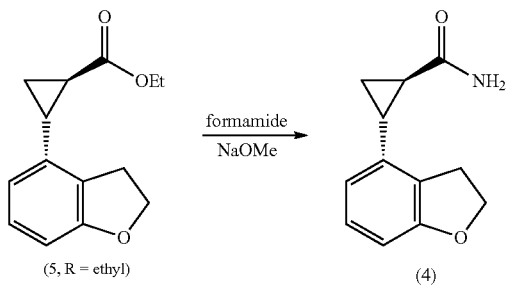

To a solution of ethyl (1R,2R)-2-(2,3-dihydro-1-benzofuran-4-yl)cyclopropane-1-carboxylate (Formula (5), R=ethyl, 8.5 g, 28.28 mmol) in formamide (15 mL) was added sodium methoxide (25 wt %) in methanol (12.2 g, 56.56 mmol) at room temperature. The resulting clear brown solution changed to a light brown suspension within 15 minutes. The light brown suspension was stirred at room temperature for 3 hours followed by heating to 45° C. and stirring for about 16 hours. Following completion of the reaction, water (40 mL) was added to the suspension at room temperature. Following 1 hour of stirring, the product was collected by filtration, washed with water (2×10 mL) water and dried in vacuo at 50-60° C. to afford (1R,2R)-2-(2,3-dihydro-1-benzofuran-4-yl)cyclopropane-1-carboxamide (Formula (4)) (4.4 g, 75.6% yield) as a beige solid, 99.9% purity by HPLC (area %).

Example 5

Preparation of (1R,2R)-2-(2,3-dihydro-1-benzo-furan-4-yl)cyclopropane-1-carboxamide (Formula (4))

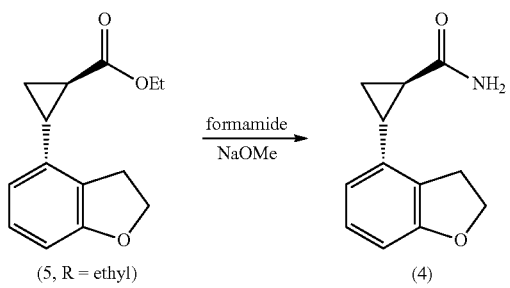

To a solution of ethyl (1R,2R)-2-(2,3-dihydro-1-benzofuran-4-yl)cyclopropane-1-carboxylate (Formula (5), R=ethyl, 8.5 g, 28.28 mmol) in formamide (25 mL) was added sodium methoxide (15 wt %) in methanol (20.4 g, 56.56 mmol) at room temperature. The resulting clear, brown solution changed to a light brown suspension within 15 minutes. The light brown suspension was heated to 45-50° C. and stirred for about 22 hours. Following completion of the reaction, water (40 mL) was added to the suspension at room temperature. Following about 1 hour of stirring, the product was collected by filtration, washed with water (2×10 mL) and dried in vacuo at 50-60° C. to afford (1R,2R)-2-(2,3-dihydro-1-benzofuran-4-yl)cyclopropane-1-carboxamide (Formula (4)) (4.1 g, 71% yield) as a beige solid, 99.8% purity by HPLC (area %).

Example 6

Preparation of (1R,2R)-2-(2,3-dihydro-1-benzo-furan-4-yl)cyclopropane-1-carboxamide (Formula (4))

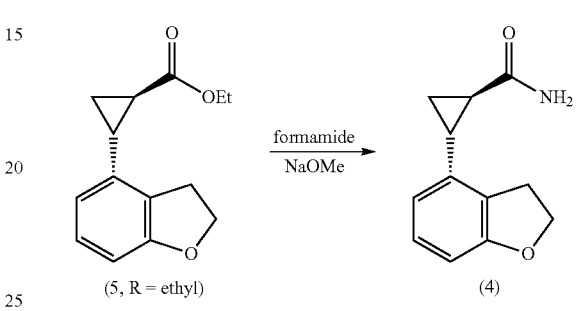

To a solution of ethyl (1R,2R)-2-(2,3-dihydro-1-benzofuran-4-yl)cyclopropane-1-carboxylate (Formula (5), R=ethyl, 8.5 g, 28.28 mmol) in formamide (25 mL) was added sodium methoxide (25 wt %) in methanol (18.3 g, 84.90 mmol) at room temperature. The resulting clear, brown solution changed to a light brown suspension within 15 minutes. The light brown suspension was heated to 45° C. and stirred for about 24 hours. Following completion of the reaction, water (40 mL) was added to the suspension at room temperature, and the suspension was stirred at room temperature for 1 hour. The product was collected by filtration, washed with water (2×10 mL) and dried in vacuo at 50-60° C. to afford (1R,2R)-2-(2,3-dihydro-1-benzofuran-4-yl)cyclopropane-1-carboxamide (Formula (4)) (4.3 g, 74.7% yield) as a beige solid, 99.9% purity by HPLC (area %).

Example 7

Preparation of (1R,2R)-2-(2,3-dihydro-1-benzo-furan-4-yl)cyclopropane-1-carboxamide (Formula (4))

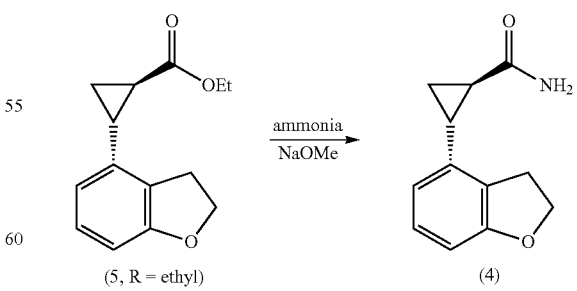

To a solution of ethyl (1R,2R)-2-(2,3-dihydro-1-benzofuran-4-yl)cyclopropane-1-carboxylate (Formula (5), R=ethyl, 0.25 g, 1.08 mmol) in methanolic ammonia (10 mL, 22.5 wt % ammonia) was added a catalytic amount of sodium methoxide (25 wt %) in methanol. The mixture was heated to 70-75° C. in a sealed vessel and stirred for about 16 hours. Following completion of the reaction, the mixture was cooled to 5-10° C. The resulting solid was collected by filtration, washed with water (2×4 mL) and dried in vacuo at 45-50° C. to afford (1R,2R)-2-(2,3-dihydro-1-benzofuran-4-yl)cyclopropane-1-carboxamide (Formula (4)) as a beige solid having >98% purity by $^1$H NMR.

Example 8

Preparation of 1-[(1R,2R)-2-(2,3-dihydro-1-benzofuran-4-yl)cyclopropyl]methanamine (1S)-(+)-10-camphorsulfonic acid salt (Formula (2-A))

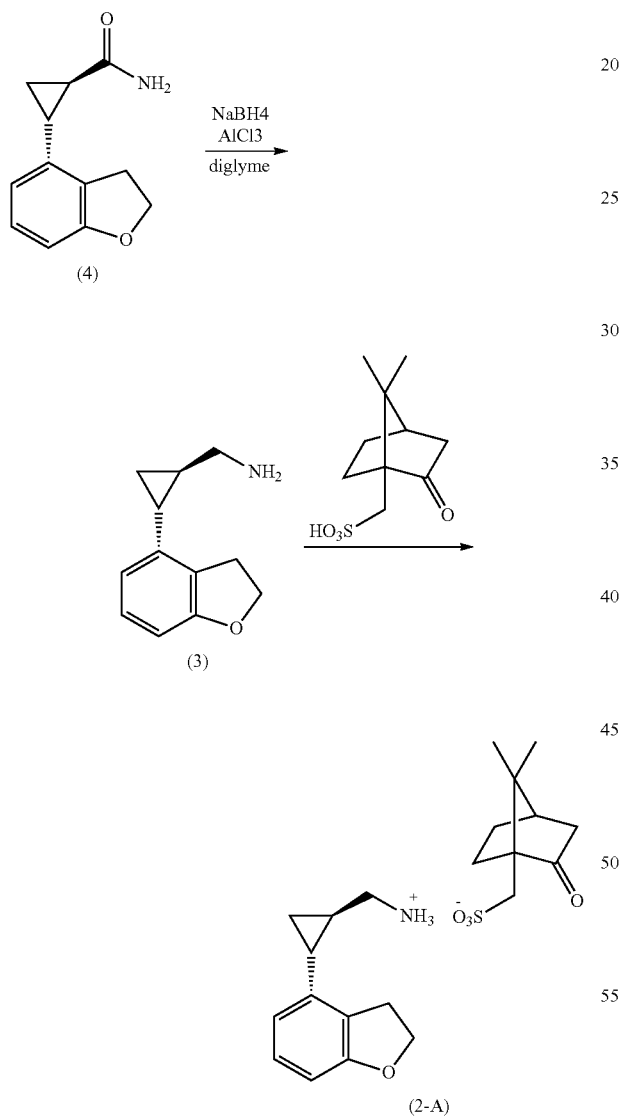

All notations of volumes are with reference to the weight of Formula (4).

A cooled (0-5° C.) suspension of (1R,2R)-2-(2,3-dihydro-1-benzofuran-4-yl)cyclopropane-1-carboxamide (Formula (4), 25.42 g, 125.1 mmol) in diglyme (125 mL) and tetrahydrofuran (75 mL) was charged with anhydrous aluminum chloride (16.67 g, 125.0 mmol) portion-wise while keeping the reaction temperature below 15° C. The resulting clear, pale yellow solution was cooled to 0-5° C., the cooling bath was removed, and then sodium borohydride (9.46 g, 250.0 mmol) was added portion-wise over 15 minutes. The reaction mixture was heated to 80-85° C. and maintained at this temperature for about 16 hours. Once completion of the reaction was confirmed by TLC, the tetrahydrofuran was distilled off, the reaction mixture was diluted with toluene (6 volumes), cooled to 0-5° C., and slowly charged with methanol (1 volume). This was followed by the slow addition of 18% hydrochloric acid (75 mL) while maintaining reaction temperature below 15° C. The reaction mixture was slowly heated to 45-50° C. and maintained for 1 hour. After cooling the reaction mixture to 0-5° C., 25% aqueous sodium hydroxide (5 volumes) was added while keeping temperature below 15° C. The reaction mixture was diluted with water (1 volume), warmed to 30-35° C., and the organic and aqueous phases were separated. The organic phase was washed with water (3 volumes). The combined aqueous phases were extracted with toluene (2×3 volumes), and the combined toluene extracts were washed with water (3 volumes). All of the organic phases were combined and concentrated.

(1S)-(+)-10-Camphorsulfonic acid (27.59 g, 118.8 mmol) was added to the concentrate (4.2 volumes, 93 g), and the mixture was stirred at room temperature for 16 hours. The resulting suspension was heated to 55-60° C. and stirred 6 hours, after which it was cooled to room temperature and filtered. The collected solid was washed twice with toluene (2×2 volumes) in vacuo at 40-45° C. to afford 1-[(1R,2R)-2-(2,3-dihydro-1-benzofuran-4-yl)cyclopropyl]methanamine (1S)-(+)-10-camphorsulfonic acid salt (Formula (2-A)) as a white solid: 46.76 g (88% yield); HPLC 99.6% (area %); chiral purity (HPLC) 98.6% R,R. $^1$H-NMR (300 MHz, DMSO-$d_6$): δ=7.88 (br s, 3H), 6.98 (appt t, J=7.8 Hz, 1H), 6.55 (appt d, J=7.8 Hz, 1H), 6.36 (appt d, J=7.7 Hz, 1H), 4.53 (appt t, J=8.8 Hz, 2H), 3.13-3.35 (m, 2H), 2.81-2.96 (m, 3H), 2.59-2.71 (m, 1H), 2.42 (appt d, J=14.7 Hz, 1H), 2.20-2.29 (m, 1H), 1.76-1.96 (m, 4H), 1.22-1.44 (m, 3H), 0.92-1.04 (m, 5H), 0.74 (s, 3H).

Example 9

Purification of 1-[(1R,2R)-2-(2,3-dihydro-1-benzofuran-4-yl)cyclopropyl]methanamine (1S)-(+)-10-camphorsulfonic Acid Salt (Formula (2-A))

The 1-[(1R,2R)-2-(2,3-dihydro-1-benzofuran-4-yl)cyclopropyl]methanamine (1S)-(+)-10-camphorsulfonic acid salt (Formula (2-A)) obtained in Example 8 (46 g) was combined with a 1:1 (v/v) solution of toluene:isopropanol (230 mL), heated to 55-60° C., and stirred for 6 hours. After cooling to room temperature, the solid product was isolated by filtration, washed with 1:1 toluene:isopropanol (2×1.5 volumes) and dried in vacuo at 45-50° C. to afford 1-[(1R,2R)-2-(2,3-dihydro-1-benzofuran-4-yl)cyclopropyl]methanamine (1S)-(+)-10-camphorsulfonic acid salt (Formula (2-A)) as a white solid: 44.54 g (97% yield); HPLC 99.8% (area %); chiral purity (HPLC) 99.8% R,R.

Example 10

Preparation of 1-[(1R,2R)-2-(2,3-dihydro-1-benzofuran-4-yl)cyclopropyl]methanamine hydrochloric acid salt (Formula (3-A))

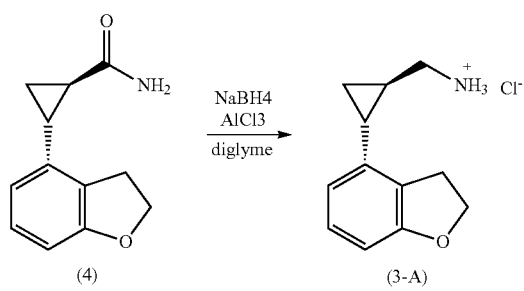

All notations of volumes are with reference to the weight of Formula (4).

A cooled (0-5° C.) suspension of (1R,2R)-2-(2,3-dihydro-1-benzofuran-4-yl)cyclopropane-1-carboxamide (Formula (4), 10.16 g, 50.0 mmol) in diglyme (50 mL) and tetrahydrofuran (30 mL) was charged with anhydrous aluminum chloride (6.66 g, 50.0 mmol), and the reaction temperature was allowed to increase to each 20° C. Sodium borohydride (3.78 g, 100.0 mmol) was then added portion-wise to the cooled (0-5° C.) clear solution while keeping reaction temperature below 15° C. The reaction mixture was then heated to 80-85° C. and maintained at this temperature for about 22 hours. Once the completion of the reaction was confirmed by TLC, the tetrahydrofuran was distilled off, toluene (6 volumes) was added, the reaction mixture was cooled to 0-5° C. and methanol (1 volume) was slowly added. This was followed by the slow addition of 18% hydrochloric acid (3 volumes) while maintaining reaction temperature below 10° C., when the reaction mixture was slowly heated to about 50° C. and maintained at this temperature for about 1 hour. After cooling the reaction mixture to below 10° C., 25% aqueous sodium hydroxide (5 volumes) was added while keeping temperature below 20° C. Following completion of the addition, the mixture was warmed to 30° C. and the organic and aqueous phases were separated. The organic phase was washed with water (3 volumes). The combined aqueous phases were extracted with toluene (2×3 volumes), and these combined toluene extracts were washed with water. All of the organic phases were combined and concentrated in vacuo. The resulting concentrate (4.2 volumes) was diluted with toluene (3 volumes), and then 14% anhydrous HCl in isopropanol (19.3 g, 74 mmol) was added, and the mixture was stirred at room temperature for 2 days. The suspension was heated to about 60° C. and stirred about 1 hour, then it was cooled to room temperature. After further cooling to 0-5° C. for about 1 hour, the product was collected by filtration, washed with toluene, and dried in vacuo at 40-45° C. to afford 1-[(1R,2R)-2-(2,3-dihydro-1-benzofuran-4-yl)cyclopropyl]methanamine hydrochloric acid salt (Formula (3-A)) as a white solid: 9.60 g (85% yield); HPLC 98.7% (area %); chiral purity (HPLC) 97.8% R,R.

Example 11

Preparation of 1-[(1R,2R)-2-(2,3-dihydro-1-benzofuran-4-yl)cyclopropyl]methanamine (1S)-(+)-10-camphorsulfonic Acid Salt (Formula (2-A))

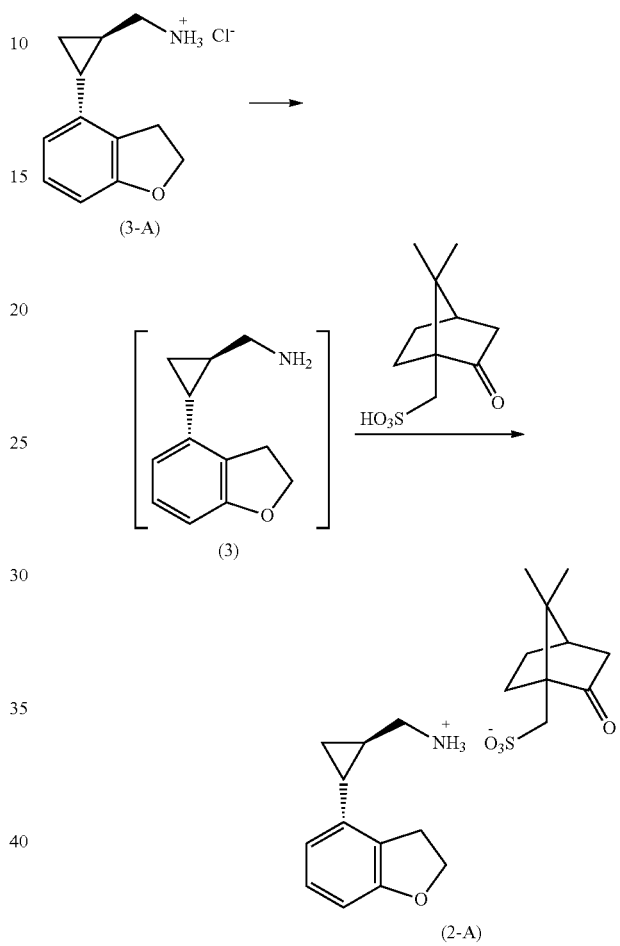

A suspension of 1-[(1R,2R)-2-(2,3-dihydro-1-benzofuran-4-yl)cyclopropyl]methanamine hydrochloric acid salt (Formula (3-A), 16.50 g, 73.1 mmol; chiral purity (HPLC), ca. 97.3% R,R) in toluene (160 mL) and water (80 mL) was charged with 5 N aqueous sodium hydroxide (16.1 mL, 80.4 mmol), and the reaction mixture was stirred for 15 minutes at room temperature. After separation of the aqueous and organic phases, the aqueous phase was extracted with toluene (80 mL), and the combined organic phases were washed with water (40 mL). The organic phase was concentrated in vacuo to a volume of about 100 mL, which was then added to a stirred solution of (1S)-(+)-10-camphorsulfonic acid (16.1 g, 69.4 mmol) in isopropanol (30 mL) at room temperature. The resulting thick suspension was heated to 55-60° C., diluted with isopropanol (20 mL) and stirred at this temperature for about 7 hours. After stirring for an additional 2 days at room temperature, the product was isolated by filtration, washed with 3:1 toluene:heptanes (30 mL) and dried in vacuo at 45-50° C. to afford 1-[(1R,2R)-2-(2,3-dihydro-1-benzofuran-4-yl)cyclopropyl]methanamine (1S)-(+)-10-camphorsulfonic acid salt (Formula (2-A)) as a white solid: 26.37 g (86% yield); HPLC 99.9% (area %); chiral purity (HPLC) 99.8% R,R.

Example 12

Preparation of 1-[(1R,2R)-2-(2,3-dihydro-1-benzofuran-4-yl)cyclopropyl]methanamine (1S)-(+)-10-camphorsulfonic Acid Salt (Formula (2))

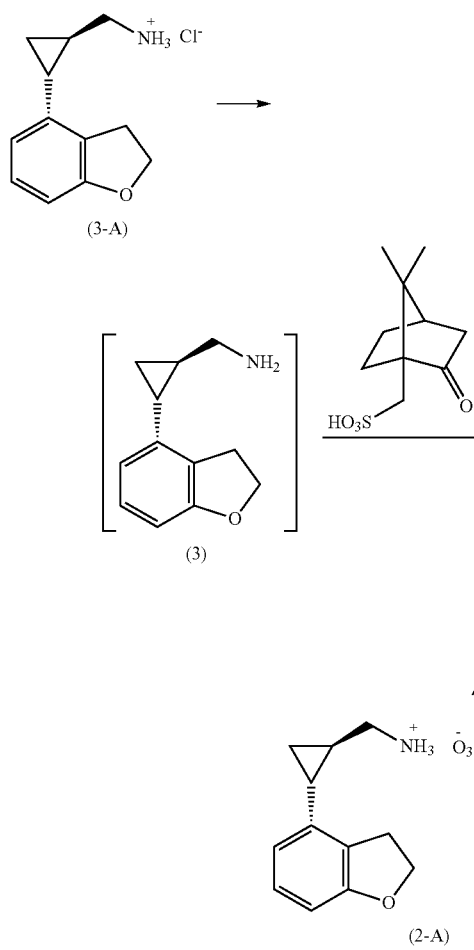

A mixture of 1-[(1R,2R)-2-(2,3-dihydro-1-benzofuran-4-yl)cyclopropyl]methanamine hydrochloric acid salt (Formula (3-A), 1.13 g, 5.0 mmol; chiral purity (HPLC), 97.3% R,R) and 5 N aqueous sodium hydroxide (1.1 mL, 5.5 mmol) in toluene (30 mL) and water (10 mL) was stirred for 40 minutes at room temperature. After separation of the organic and aqueous phases, the aqueous phase was extracted with toluene (10 mL), and the combined organic phases were washed with water (10 mL). The separated organic phase was added to a stirred solution of (1S)-(+)-10-camphorsulfonic acid (1.09 g, 4.7 mmol) in methanol (5 mL) at room temperature. The resulting thick suspension was heated to 60-65° C. and stirred at this temperature for about 1 hour, then at room temperature for 20 additional hours. The resulting product was isolated by filtration, washed with toluene (5 mL) and dried in vacuo at 45-50° C. to afford 1-[(1R,2R)-2-(2,3-dihydro-1-benzofuran-4-yl)cyclopropyl] methanamine (1S)-(+)-10-camphorsulfonic acid salt (Formula (2-A)) as a white solid: 1.43 g (68% yield); chiral purity (HPLC) 100.0% R,R.

Example 13

Preparation of 1-[(1R,2R)-2-(2,3-dihydro-1-benzofuran-4-yl)cyclopropyl]methanamine (1S)-(+)-10-camphorsulfonic Acid Salt (Formula (2))

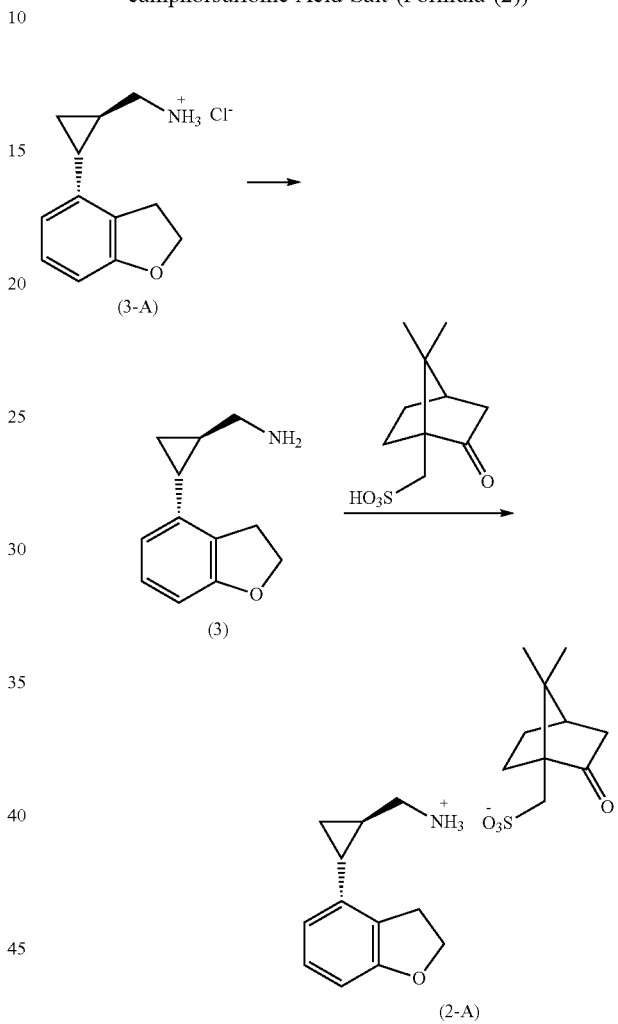

All notations of volumes are with reference to the weight of Formula (3-A).

A suspension of 1-[(1R,2R)-2-(2,3-dihydro-1-benzofuran-4-yl)cyclopropyl]methanamine hydrochloric acid salt (Formula (3-A), 10.35 g, 45.85 mmol; chiral purity (HPLC), 97.5% R,R) in toluene (10 volumes) and water (5 volumes) was charged with sodium hydroxide (2.02 g, 50.5 mmol), and the reaction mixture was stirred for 40 minutes at room temperature. The organic and aqueous phases were separated, the aqueous phase was extracted with toluene, and the combined organic phases were washed with water. The organic phase was concentrated in vacuo to a residue (8.34 g), which was dissolved in toluene (3 volumes) and the solution divided into two equal portions. One portion (16.3 g) was diluted with toluene (3 volumes with respect to the portion) and diglyme (8 g), and then (1S)-(+)-10-camphorsulfonic acid (5.12 g, 22.0 mmol) was added. The thick mixture was diluted with toluene (8 mL), heated to 55-60°

C. and stirred overnight. The product was isolated by filtration, washed with toluene and dried in vacuo to afford 1-[(1R,2R)-2-(2,3-dihydro-1-benzofuran-4-yl)cyclopropyl]methanamine (1S)-(+)-10-camphorsulfonic acid salt (Formula (2-A)) as a white solid: 8.57 g (89% yield); HPLC 99.4% (area %); chiral purity (HPLC) 99.6% R,R.

Example 14

Preparation of N-{[(1R,2R)-2-(2,3-dihydro-1-benzofuran-4-yl)cyclopropyl]methyl}propanamide (Tasimelteon, Formula (1))

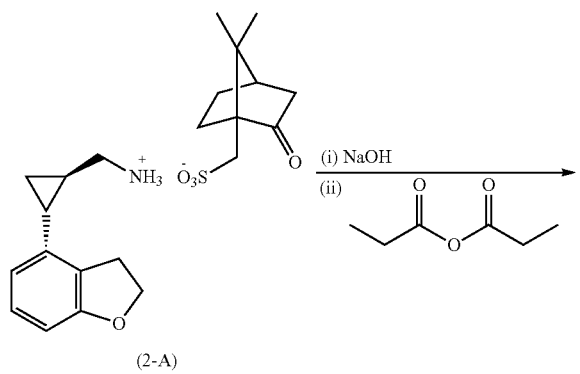

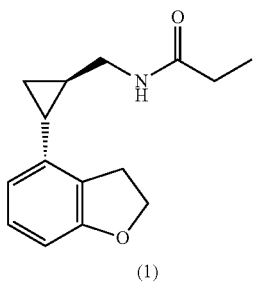

A suspension of 1-[(1R,2R)-2-(2,3-dihydro-1-benzofuran-4-yl)cyclopropyl]methanamine (1S)-(+)-10-camphorsulfonic acid salt (Formula (2-A), 29.50 g, 69.98 mmol; chiral purity (HPLC), 99.8% R,R) in toluene (150 mL) and water (150 mL) was charged with sodium hydroxide (6.16 g, 154.0 mmol), and the reaction mixture was stirred for 1.5 hours at room temperature. The clear, biphasic mixture was then cooled to 0-5° C. and propionic anhydride (10.02 g, 76.98 mmol) was added (over 10 minutes) while maintaining the temperature below 10° C. Stirring at 0-10° C. was continued for 20 minutes until completion of the reaction as measured by TLC. After warming the reaction mixture to room temperature and separation of the aqueous and organic phases, the aqueous phase was extracted with toluene (90 mL) and the combined organic phases were washed with water (2×60 mL). The organic phase was concentrated in vacuo to a volume of about 90 mL, diluted with toluene (30 mL) and clarified with a toluene rinse (60 mL). The combined filtrate was concentrated in vacuo to a volume of about 90 mL, at which time heptanes (30 mL) was added to the stirred (25-30° C.) residue. The resulting thick suspension was diluted with heptanes (90 mL), stirred at room temperature for 16 hours and then at 0-5° C. for 3 hours. The product was isolated by filtration, washed with heptanes (60 mL) and dried in vacuo at 40-45° C. to afford N-{[(1R,2R)-2-(2,3-dihydro-1-benzofuran-4-yl)cyclopropyl]methyl}propanamide (Formula (1)) as a white solid: 16.29 g (95% yield); HPLC 99.8% (area %); chiral purity (HPLC) 100.0% R,R.

Example 15

Preparation of N-{[(1R,2R)-2-(2,3-dihydro-1-benzofuran-4-yl)cyclopropyl]methyl}propanamide (Formula (1) Tasimelteon)

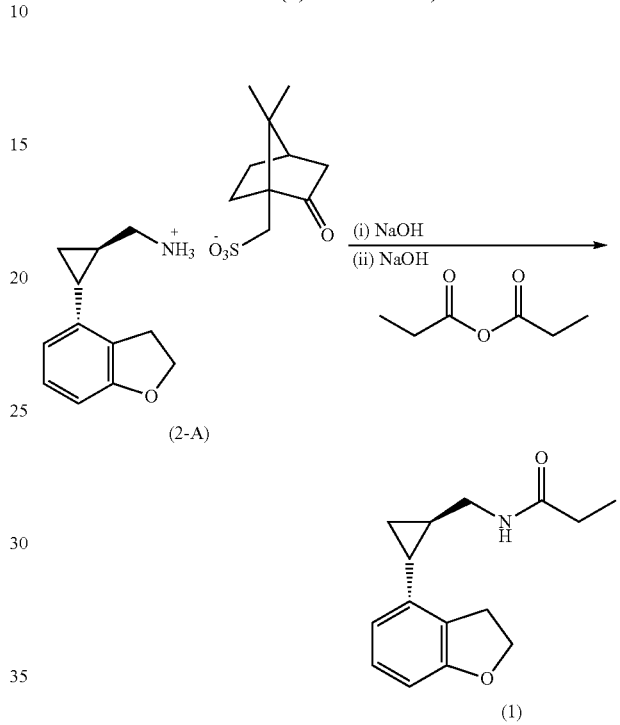

All notations of volumes are with reference to the weight of Formula (2-A).

A mixture of 1-[(1R,2R)-2-(2,3-dihydro-1-benzofuran-4-yl)cyclopropyl]methanamine (1S)-(+)-10-camphorsulfonic acid salt (Formula (2-A), 8.35 g, 19.81 mmol; chiral purity (HPLC), 99.6% R,R) and sodium hydroxide (0.87 g, 21.8 mmol) in toluene (8 volumes) and water (8 volumes) was stirred at room temperature for about 1 hour. The aqueous phase of the reaction mixture was separated and discarded. The remaining organic phase was charged with water (8 volumes) and the mixture cooled to 0-5° C. Sodium hydroxide (0.87 g, 21.8 mmol) and then propionic anhydride (3.09 g, 23.8 mmol) were added, with stirring at 0-5° C. continued for 10 minutes. After warming the reaction mixture to room temperature, the organic and aqueous phases were separated, with the organic phase being washed with water (2 volumes). The combined aqueous phases were extracted with toluene (2 volumes). The combined organic phases were concentrated in vacuo leaving a residue, which was combined with toluene (2 volumes) and then heptanes (2 volumes). After stirring for half an hour, the resulting suspension was diluted with a mixture of toluene (2 volumes) and heptanes (4 volumes), and stirred at room temperature overnight. The suspension was then heated to 40-45° C., slowly cooled to room temperature and stirred overnight. The resulting product was isolated by filtration, washed with heptanes (4 volumes) and dried in vacuo affording N-{[(1R,2R)-2-(2,3-dihydro-1-benzofuran-4-yl)cyclopropyl]methyl}propanamide (Formula (1)) as a white solid: 4.0 g (82% yield); HPLC 99.7% (area %); chiral purity (HPLC) 100.0% R,R.

Example 16

Preparation of N-{[(1R,2R)-2-(2,3-dihydro-1-benzofuran-4-yl)cyclopropyl]methyl}propanamide (Formula (1) Tasimelteon)

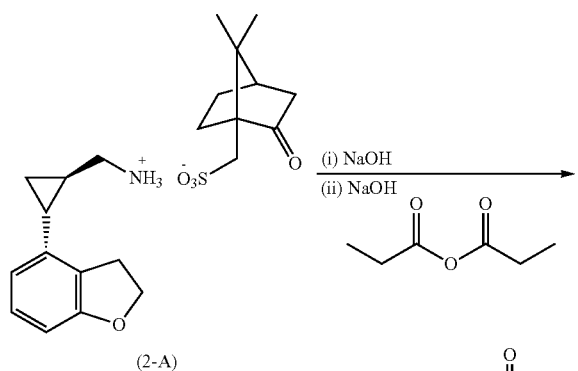

A mixture of 1-[(1R,2R)-2-(2,3-dihydro-1-benzofuran-4-yl)cyclopropyl]methanamine (1S)-(+)-10-camphorsulfonic acid salt (Formula (2-A) 5.06 g, 12.0 mmol; chiral purity (HPLC), 99.7% R,R) and sodium hydroxide (0.53 g, 13.2 mmol) in toluene (25 mL) and water (25 mL) was stirred at room temperature for about 1 hour. The aqueous phase of the reaction mixture was separated and discarded. The remaining organic phase was charged with water (25 mL), sodium hydroxide (0.53 g, 13.2 mmol) and propionic anhydride (1.72 g, 13.2 mmol), cooled in an ice-water bath and stirred about 10 minutes. After warming the reaction mixture to room temperature, the organic and aqueous phases were separated, the aqueous phase was extracted with toluene (15 mL), and the combined organic phases were washed with water (2×10 mL). The organic phase was concentrated in vacuo leaving a residue, which was combined with 1:1 toluene:heptanes (7 mL) and heated briefly, during which time a precipitate formed. The resulting suspension was diluted with 1:2 toluene:heptanes (about 10 mL) and stirred at room temperature overnight. The product was isolated by filtration, affording N-{[(1R,2R)-2-(2,3-dihydro-1-benzofuran-4-yl)cyclopropyl]methyl}propanamide (Formula (1)) as a white solid: 2.73 g (93% yield); HPLC 99.5% (area %).

Example 17

Preparation of N-{[(1R,2R)-2-(2,3-dihydro-1-benzofuran-4-yl)cyclopropyl]methyl}propanamide (Formula (1) Tasimelteon)

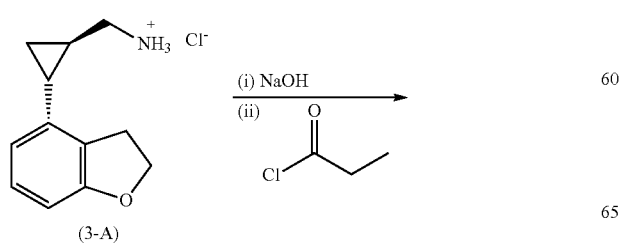

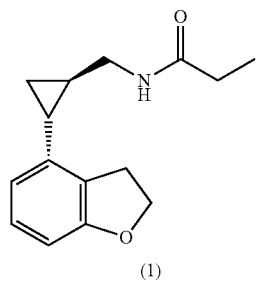

To a mixture of 1-[(1R,2R)-2-(2,3-dihydro-1-benzofuran-4-yl)cyclopropyl]methanamine hydrochloric acid salt (Formula (3-A), 1.0 g, 4.44 mmol) in toluene (5 mL) and water (5 mL) at 0-5° C. was added sodium hydroxide (25 wt %, 9.3 mmol), followed by drop-wise addition of propionyl chloride (0.4 g, 4.52 mmol). Following addition, the reaction mixture was stirred for a further period of 15 minutes before warming to room temperature. Toluene (15 mL) was added and the phases separated. The organic layer was washed with water (10 mL) and evaporated to dryness. The dried residue was crystallized from toluene:heptanes (2:3 ratio, 10 mL), filtered and dried to afford 0.98 g N-{[(1R,2R)-2-(2,3-dihydro-1-benzofuran-4-yl)cyclopropyl]methyl}propanamide (Formula (1)).

What is claimed is:

1. A process for preparing a compound of Formula (1)

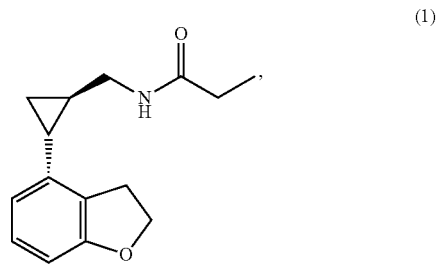

the process comprising:
 (i) reacting a compound of Formula (3)

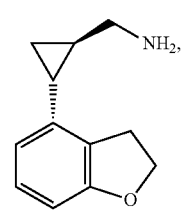

with (S)-(+)-camphorsulfonic acid in a suitable solvent to form a salt of Formula (2-A)

(2-A)

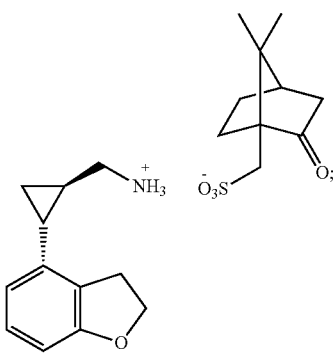

(ii) isolating the salt of Formula (2-A) formed in step (i);
(iii) treating the salt of Formula (2-A) with a first base to produce a compound of Formula (3), wherein the purity of the compound of Formula (3) formed in step (iii) is greater than the purity of the compound of Formula (3) used in step (i); and
(iv) reacting the compound of Formula (3) prepared in step (iii) with a compound of Formula (A)

(A)

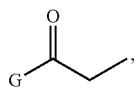

wherein G is a leaving group.

2. The process of claim 1, wherein the purity in step (iii) is chemical purity.

3. The process of claim 1, wherein the purity in step (iii) is chiral purity.

4. The process of claim 1, wherein the solvent comprises toluene.

5. The process of claim 1, wherein the solvent comprises a mixture of toluene and a second solvent.

6. The process of claim 5, wherein the second solvent is selected from the group consisting of diglyme, 2-propanol and methanol.

7. The process of claim 1, wherein the salt of Formula (2-A) obtained in step (ii) is further purified prior to step (iii).

8. The process of claim 7, wherein the salt of Formula (2-A) obtained in step (ii) is purified by stirring a slurry of the salt of Formula (2-A) in a solvent comprising a $C_1$-$C_3$ alcohol prior to isolating the salt of Formula (2-A) by filtration.

9. The process of claim 1, wherein the reaction of the compound of Formula (3) with the compound of Formula (A) occurs in the presence of a second base.

10. The process of claim 9, wherein the second base is the same as the first base used in step (iii), and is a tertiary amine or a metal hydroxide.

11. The process of claim 1, wherein the compound of Formula (A) is propionic anhydride.

12. The process of claim 1, wherein the compound of Formula (3) is prepared by a process comprising reducing a compound of Formula (4):

(4)

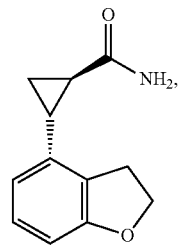

with sodium borohydride in the presence of aluminum trichloride and diglyme.

13. The process of claim 12, wherein diglyme is used with a co-solvent.

14. The process of claim 13, wherein tetrahydrofuran is used as the co-solvent.

15. The process of claim 12, wherein the compound of Formula (4) is prepared by a process comprising reacting a compound of Formula (5):

(5)

wherein R is a $C_1$-$C_4$ alkyl chain, with either of:
(a) methanolic ammonia; or
(b) a mixture of formamide and metal alkoxide.

16. The process of claim 15, wherein the compound of Formula (5) is reacted with a mixture of formamide and metal alkoxide.

17. The process of claim 16, wherein the metal alkoxide is sodium methoxide.

18. The process of claim 15, wherein R in the compound of Formula (5) is ethyl.

19. The salt of Formula (2-A):

(2-A)

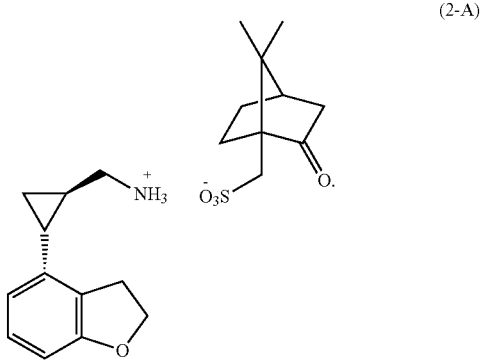

20. A process for preparing a salt of Formula (2-A)
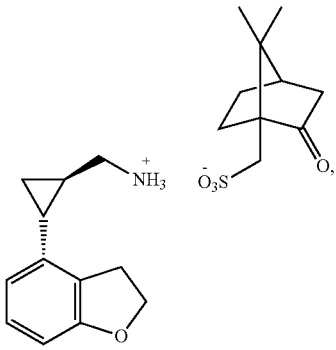
(2-A)
the process comprising the steps of:
(i) reacting a compound of Formula (3)
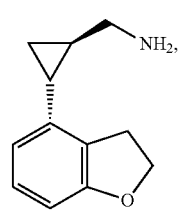
(3)
with (S)-(+)-camphorsulfonic acid in a suitable solvent; and
(ii) isolating a salt of Formula (2-A) formed between the compound of Formula (3) and (S)-(+)-camphorsulfonic acid.
* * * * *